(12) United States Patent
Tajima

(10) Patent No.: US 6,691,748 B1
(45) Date of Patent: Feb. 17, 2004

(54) CONTAINER TRANSFER AND PROCESSING SYSTEM

(75) Inventor: Hideji Tajima, Matsudo (JP)

(73) Assignee: Precision System Science Co., Ltd., Chiba (JP)

( * ) Notice: Subject to any disclaimer, the term of this patent is extended or adjusted under 35 U.S.C. 154(b) by 0 days.

(21) Appl. No.: 10/181,582

(22) PCT Filed: Jan. 16, 2001

(86) PCT No.: PCT/JP01/00224

§ 371 (c)(1),
(2), (4) Date: Sep. 17, 2002

(87) PCT Pub. No.: WO01/53839

PCT Pub. Date: Jul. 26, 2001

(30) Foreign Application Priority Data

Jan. 17, 2000 (JP) ........................................ 2000-007279

(51) Int. Cl.$^7$ ................................................ B65B 1/04
(52) U.S. Cl. .................. 141/130; 422/99; 422/100; 436/47; 73/864.11
(58) Field of Search ............................ 141/130; 422/99, 422/100, 67; 436/47; 73/864.11, 864.13, 864.24, 864.25

(56) References Cited

U.S. PATENT DOCUMENTS 5,518,686 A * 5/1996 Masterson et al. ............ 422/63
6,006,800 A * 12/1999 Nakano ....................... 141/130
6,325,114 B1 * 12/2001 Bevirt et al. ................. 141/130

FOREIGN PATENT DOCUMENTS

JP 59-84159 5/1984
JP 62-237342 10/1987

(List continued on next page.)

OTHER PUBLICATIONS

Shuji, Tajima, "Jiseitai Biryushi ni yoru Kakusan Bunri Chuushitsu no Jidouka", Nippon Ouyou Jiki Gakkaishi, 1998, vol. 22, No. 5, (Japan) pp. 1010–1015.

(List continued on next page.)

*Primary Examiner*—Steven O. Douglas
(74) *Attorney, Agent, or Firm*—Haynes and Boone, LLP

(57) ABSTRACT

An object is to provide a container transfer and processing system which can simplify total construction and control, does not increase time and cost in manufacturing and use, which is easy to use, and which runs efficiently, and for which processing of large quantities of containers can be performed rapidly and easily.

The container transfer and processing system has; a turntable capable of mounting a specified quantity of plate-shaped containers or tip racks, and simultaneously transferring in both a forward and reverse direction along a circular route, a plurality of container working devices arranged in an area outside of the route of the turntable and along the route direction, for performing various kinds of operations on the containers mounted on the turntable or the contents thereof or containers mounted at predetermined positions outside of the turntable or the contents thereof, a robot provided in an inside area surrounded by the route, having a holding part capable of holding the containers or the tip racks, and an arm connected to the holding part and capable of moving the holding part between arbitrary positions inside an area including mounting positions of the containers on the turntable and on the sets of container working devices, and a control part for performing transfer of the turntable, operation of the sets of container working devices, and control of the robot; and the plurality of sets of container working devices are; a dispensing apparatus, a magnetic particle integratedly processing apparatus, a constant temperature apparatus for cooling or heating, a stacking apparatus for stacking the containers or the tip racks, a reagent supplying apparatus, a container washing apparatus, a nozzle tip washing apparatus and a measuring apparatus for measuring the contents of the containers.

37 Claims, 12 Drawing Sheets

FOREIGN PATENT DOCUMENTS

| | | |
|---|---|---|
| JP | 64-6760 | 1/1989 |
| JP | 4-350561 | 12/1992 |
| JP | 5-312815 | 11/1993 |
| JP | 6-277036 | 10/1994 |
| JP | 6-308133 | 11/1994 |
| JP | 8-211071 | 8/1996 |
| JP | 9-96641 | 4/1997 |
| JP | 11-72369 | 3/1999 |

OTHER PUBLICATIONS

ISA/Japanese Patent Office, International Search Report for PCT/JP02/00224, dated Apr. 17, 2001, 3 pages.

International Preliminary Examination Report, IPEA/JP, dated Sep. 11, 2001, 3 pages.

* cited by examiner (a)

(b)

CONTAINER TRANSFER AND PROCESSING SYSTEM

This application is a national phase filing of international application No. PCT/JP01/00224, filed Jan. 16, 2001, which claims priority to Japanese patent application No. 2000-7279, filed Jan. 17, 2000.

TECHNICAL FIELD

The present invention relates to a container transfer and processing system. The present invention relates to fields which require a variety of chemical reaction processing such as the engineering field, the agricultural field of the food industry, agricultural products industry and marine products industry, etc., the pharmaceutical field, the medical field of hygienics, health, immunization, disease, genetics, etc., being the so called fields of science such as chemistry or biology and the like. The present invention particularly relates to a container transfer and processing system which has high processing ability (high-throughput) by loading plate-shaped containers each having a specified quantity of storage parts, in order to efficiently and rapidly perform processing for DNA, immunization, chemical reactions and the like.

BACKGROUND ART

Heretofore, as shown in FIG. 12, there has been a sets of container working devices 200 for processing a large quantity of containers, while the containers are being transferred in-line using only robots.

This apparatus 200 as shown in the figure, has an elongate mounting part 201 for mounting plate-shaped containers 11, a robot 202 which is movable along the mounting part 201, and which grasps a container 11 which is mounted on the mounting part 201, and which is able to transport the container 11 within the mounting part 201 while following along the longitudinal direction of the mounting part, and to outside the mounting part 201 while following perpendicular to the longitudinal direction, and a number of various types of work devices 203, 204, 205, 206, 207, 208 and 209 for performing various operations on the containers, which are arranged along the longitudinal direction of the mounting part 201.

The above-mentioned robot 202 has a movable part 211 which moves on a rail 201 laid along the longitudinal direction of the mounting part 201, a polar coordinate type arm 212, and the holding part 213 which is connected to the arm 212.

Reference symbol 204 denotes a plate stacker for stacking plate-shaped containers, reference symbols 205 and 206 denote dispensers, reference symbol 207 denotes a thermal cycler, reference symbol 208 denotes a dispenser and reference symbol 209 denotes a plate reader.

Moreover, heretofore there has been a transferring device for transferring a large number of mounted containers all together in line in one direction, and a processing apparatus (not shown) with various work devices aligned along the route of the transferring device, which does not use a robot capable of transferring containers between optional locations.

Incidentally, in the former apparatus of the processing apparatus related the above described prior art, one robot can only individually transfer one container at a time. Therefore this has a problem in that while a robot is transferring a container to a certain processing apparatus, the transfer process for the other containers cannot be performed. Hence, no matter how high the processing ability for the various kinds of processing apparatus, the processing ability or the processing speed for the whole apparatus is limited by the transfer ability of the robot, so that the operation overall cannot be performed rapidly or efficiently.

On the other hand, with an apparatus which transfers a number of containers all together by a linearly aligned transferring device, with various kinds of work devices arranged along the transfer device, since this transfers the containers in only one direction, the construction is such that once a container has passed through the various types of working devices it cannot return. Therefore the construction must be such that the container is not advanced until the process for transfer to the various types of working devices has been completed.

Furthermore, in transferring the containers all together, the time required for each kind of operation generally varies. Therefore in the method of transferring all containers at once, the transfer must be synchronized with each operation. Hence this has a problem in that the transfer is limited by the operation taking the longest time, so that the overall operation cannot be performed rapidly or efficiently.

Especially, if there is a process such as incubation which requires an exceptionally long time compared to other operations, the line is held up at that place, so that wasteful waiting time is increased which can have a large influence on process ability. Furthermore this has a problem in that once an accident such as a failure occurs at a process, subsequent processing becomes impossible, and the overall operation is stopped, resulting in a loss of reliability.

Moreover there is a problem in that both of these apparatus are difficult to control automatically, because operation times are not constant but changeable, and hence scheduled process time cannot be defined. Furthermore, both apparatus have a problem in that total process time is a summation of the process times at each process location, and hence the total process ability decreases rapidly with increasing processing quantity.

Therefore transfer control for both apparatus, which takes into consideration complete processes where continuous consistent steps are not allowed any lack of correspondence, as well as the output and input timing, becomes necessary. Therefore, extremely complicated software and hardware is required.

The present invention is for solving the above-mentioned technical problems, with a first object being to provide a container transfer and processing system which can simplify the total construction and control, does not increase time and cost in manufacturing and use, which is easy to use, and which runs efficiently, by skillfully combining; standardized, uniform or regular transport of large quantities along a set route, individual, arbitrary or irregular transport, and free selection of operations inside or outside the route.

A second object is to provide a container transfer and processing system for which respective operations can be easily scheduled and controlled and easily handled, with minimal influence between operations due to the amount and operation time of other operations, by skillfully combining; standardized, uniform or regular transport of large quantities along a set route, individual, arbitrary or irregular transport, and free selection of operations inside or outside the route.

A third object is to provide a highly reliable container transfer and processing system which, even in the case where an accident such as a failure occurs, can keep the influence thereof to a minimum, and immediately take measures to deal with the accident, and which can reliably handle operations, by skillfully combining; standardized, uniform or regular transport of large quantities along a set route, individual, arbitrary or irregular transport, and free selection of operations inside or outside the route.

A fourth object is to provide a flexible, extendable and general-purpose container transfer and processing system which can be modified such as by simply increasing the processing apparatus, without performing basic modification of the construction, by skillfully combining; standardized, uniform or regular transport of large quantities along a set route, individual, arbitrary or irregular transport, and free selection of operations inside or outside the route.

A fifth object is to provide a container transfer and processing system having diversity which can perform processing of objects in a variety of ways and for which various processes are possible, by skillfully combining standardized, uniform or regular transport of large quantities along a set route, individual, arbitrary or irregular transport, and free selection of operations inside or outside the route.

A sixth object is to provide a container transfer and processing system which can perform a large amount of processing rapidly and easily, by skillfully combining; standardized, uniform or regular transport of large quantities along a set route, individual, arbitrary or irregular transport, and free selection of operations inside or outside the route.

DISCLOSURE OF THE INVENTION

A first aspect of the invention to solve these technical problems is a container transfer and processing system comprising; a simultaneous transfer device capable of mounting a specified quantity of plate-shaped containers each having a specified quantity of storage parts, or a specified quantity of tip racks each storing a specified quantity of pipette tips, and simultaneously transferring along a specified route, a set of container working devices for performing various types of operations on the containers or container contents, which are within the route, or the containers or container contents which are outside of the route, an individual transfer device capable of individually transferring the containers or the tip racks between arbitrary positions inside an area including the mounting positions of the container on the route of the simultaneous transfer device and on the set of container working devices, and a control part for performing transfer of both of the transfer devices and control of the operation of the set of container working devices.

Hereupon "plate-shaped containers having a specified quantity of storage parts" is containers having for example 48, 96 or 384 storage parts (wells). Storage parts which are arranged in matrix form are called micro-plates. Furthermore "tip racks each storing a specified quantity of pipette tips" store pipette tips which in use are fitted to or detached from the set of container working devices. The number and arrangement of the tip racks depends on the number and arrangement of the nozzles of each set of container working devices. Transfer of the tip racks becomes necessary when the set of container working devices contain a dispenser or a magnetic particle integratedly processing apparatus of a type which uses removable pipette tips. This is not necessary in the case where the dispenser or the magnetic particle integratedly processing apparatus are of the nozzle wash and reuse type. "Mounting a specified quantity" is determined arbitrarily depending upon the size of the containers or tip racks, the route length, the number able to be processed, the transfer speed, and so on.

Furthermore, "a set of container working devices" is suitably selected corresponding to the contents of the processing performed in the container transfer and processing system. For example, in the case of DNA extraction, this is a dispensing apparatus (a disposable tip type or a wash and reuse type which can dispense and stir samples or reagents and suck, transfer and dispense these to other containers) having 8 heads, 12 heads, or 96 heads, a reagent bath, a constant temperature apparatus (which can be set to a plurality of conditions between 0° C. and 96° C.), a luminescence detector (a plate reader for chemiluminescence, absorbency, fluorescence etc.) and so on. In the case of immunity measurement, addition of a washer etc. is further required.

For DNA functional analysis and the like, a large number of containers and pipette tips are necessary. In addition to the above-mentioned apparatus, there is required a stacking apparatus such as a reaction plate, a tip rack and the like, an automatic supply unit for supplying a large number of containers and dispensing tips, a PCR thermal cycler, a PCR product purifier, and a sequence product creating apparatus. In the case where magnetic particles are used, a magnetic particle integratedly processing apparatus is added, so that the magnetic particles inside the plate-shaped container can be collectively stirred, washed, separated and transferred. "The magnetic particle integratedly processing apparatus", as with the before-mentioned container storage parts, has nozzles arranged in matrix form for sucking and discharging liquid, and tips removably mounted onto the nozzles. Moreover this has a magnetic part which can apply or remove a magnetic field to or from inside the tips. Controlling the "transfer" of the simultaneous transfer device and the individual transfer device by the control part includes instruction and control of; stopping, transfer speed, transfer and stopping time, transfer cycle, transfer and stopping timing, and positions of transferring and stopping.

According to the present invention, a simultaneous transfer device capable of simultaneously transferring a large quantity of plate-shaped containers, and an individual transfer device capable of individually transferring the containers between arbitrary positions where the containers can be mounted, are used in combination. Thus it is possible to transfer a large number of containers simultaneously between each kind of sets of container working devices by using the simultaneous transfer device, which is suitable for regular transfer processing of large quantities uniformly, but which cannot transfer and process a variety of types individually. Moreover, it is also possible to individually transfer containers to arbitrary positions corresponding to the contents of the operation or the circumstances of the operation, by using the individual transfer device capable of flexible transfer and processing of containers individually in various types and non-periodically, but which is not suitable for transfer and processing of large numbers. Therefore, it is possible to perform processing of a large quantity efficiently and rapidly by the simultaneous transfer device. Furthermore, it is also possible to perform positive processing efficiently with minute attention and high reliability, corresponding to the operation contents for each container, or according to individual flexibility such as for the case where it is necessary to modify the process corresponding to various situations such as an accident, a fault or a special case, without overall influencing the transfer sequence or transfer time determined in relation to the large quantity of containers, set by the simultaneous transfer device.

For example, regarding operations which take time, such as incubation, these are not performed on the transfer route by the simultaneous transfer device, but are performed outside of the transfer route, and container transfer between containers at arbitrary position inside the route and mounting positions of the set of container working devices which perform the above-mentioned operations, is performed by the individual transfer device. As a result, operation efficiency can be improved, because other operations are not limited by operations such as incubation.

Furthermore, for a container where the operation is delayed by an accident, this is transferred to outside the route, and for the other containers these are uniformly transferred by the simultaneous transfer device and the other operations are performed preferentially, thus preventing a set back to the operations of a large number of containers due to the delay of the operation of a small number of containers, and enabling efficient processing to be performed.

Moreover, according to the present invention, because the individual transfer device is capable of transferring between arbitrary positions in a whole area including the route of the simultaneous transfer device, it is not necessary to multiply set special transfer devices such as for only transferring between certain positions. Hence this contributes to a simplification of construction and a decrease in work space.

Therefore, by combining the simultaneous transfer device and the individual transfer device, it is possible to make up for various defects, and perform meticulous operations in large quantities and of various types efficiently and rapidly.

Since it is only necessary to provide one or a few individual transfer devices (no more than the number of sets of container working devices is sufficient) which are able to transfer between arbitrary positions, rather than multiply providing transfer devices between a large number of specific positions, simplification of the construction can be achieved.

By providing an individual transfer device to enable alternative route transfer for the transfer routes of the simultaneous transfer device, safety and reliability of transfer can be increased.

Moreover, according to the present invention, by providing the individual transfer device, it is possible to perform operations on containers in arbitrary sequence without limiting the position or sequence along a transfer route of the simultaneous transfer device for the set of container working devices. Therefore sequential operations can be performed from positions where operations are possible, to comply with the operation circumstances, and hence efficient processing can be performed at high speed.

A second aspect of the invention is that, in the first aspect, the route of the simultaneous transfer device is closed, and the transfer direction is in both the forward and reverse directions along the route, and the individual transfer device is a robot which is provided in an inside area enclosed within the route, and which has a holding part capable of holding the container or the tip racks, and an arm capable of moving the holding part within the area.

Here, "a closed route" is a route formed for example in a circle or doughnut shape. A simultaneous transfer device for which the route is a loop is specifically called a turntable. Moreover, the arm of the robot is for example, a polar coordinate type or an articulated type having more than one joint. Furthermore, the holding part is constructed so as to have for example, a horizontally attached plate member and a clamping element provided beneath the plate member, for holding the container tightly from both sides.

According to the second aspect of the invention, the route of the simultaneous transfer device is closed. Consequently, containers for which processing has been completed, can be returned automatically to their initial positions. Therefore, it is not necessary for the individual transfer device or a person to return the containers to their initial positions, and hence processing procedures are simplified. Furthermore, according to the present invention, a commercial robot can be used as the individual transfer device, and hence low cost manufacture is possible.

A third aspect of the invention is that in the first aspect of the invention, the set of container working devices perform a variety of operations such as; stacking the containers or the tip racks, dispensing into containers, supplying reagents for dispensing into containers, mixing and stirring in a container, separating the contents of a container, heating containers, washing containers, measuring related to the contents of a container, cleaning solution passages which have been inserted into containers, and so on.

According to the third aspect of the invention, the set of container working devices are for performing stacking etc. of the containers. As such, a variety of processes can be performed for the containers.

A fourth aspect of the invention is that, in the first aspect of the invention, one of the sets of container working devices is a dispensing apparatus, and the other sets of container working devices have one or two or more apparatus selected from; a magnetic particle integratedly processing apparatus, a measurement apparatus, a constant temperature apparatus for cooling or heating, a stacking apparatus for the containers or the tip racks, a reagent supplying apparatus, a separator, an apparatus or a container for precipitating, and a liquid passage washing apparatus.

According to the fourth aspect of the invention, an effect the same as that described for the third aspect of the invention is demonstrated.

A fifth aspect of the invention is that in the second aspect of the invention, the robot has a rotation shaft and a vertical motion shaft, both following along directions perpendicular to a transfer face of the simultaneous transfer device, within an area of the transfer device.

According to the fifth aspect of the invention, the robot is axially supported so as to hold the rotation shaft along a direction perpendicular to a transfer face of the transfer device. Therefore for the whole transfer route, simple transfer is possible by rotation of the robot.

A sixth aspect of the invention is that, in the fifth aspect of the invention, the route of the simultaneous transfer device is formed in a circular shape, and the rotation shaft of the robot is provided concentric with a center of rotation of the simultaneous transfer device.

In the sixth aspect of the invention, since the route of the simultaneous transfer device is formed in a circular shape, and the rotation shaft of the robot is coincident with the center of rotation of the simultaneous transfer device, manufacture is facilitated, and control such as for positioning depends only on rotational angle, making control easy.

A seventh aspect of the invention is that, in either of the second or the fifth aspects of the invention, the robot is provided so as to be movable along a route direction of the simultaneous transfer device, within an area inside of the simultaneous transfer device.

Here, the present invention, different from the sixth aspect of the invention, is suitable for the case where the route of the simultaneous transfer device is longer, and the number of containers being handled is large.

In the seventh aspect of the invention, the robot is provided so as to be movable along the route direction of the simultaneous transfer device, within an area inside of the transfer device. Therefore even in the case where the transfer route of the simultaneous transfer device is large, this can be coped with using one robot. Hence this contributes to simplification of construction and a decrease in manufacturing cost.

An eighth aspect of the invention is that in the fourth aspect of the invention, the dispensing apparatus has a dispenser having a plurality of liquid passages inside of which liquid passes, a magnetic force part for exerting and removing a magnetic field onto and from the liquid passages from outside, a pressure controller for controlling the pressure inside the liquid passages to suck and discharge liquid, and a moving part for relatively moving between the dispensing apparatus or the liquid passages and the containers.

In the eighth aspect of the invention, a dispensing apparatus capable of exerting a magnetic force on the liquid passage interior is provided at one of the sets of container working devices. Therefore a process using magnetic particles can also be performed, and hence a variety of processes can be efficiently performed.

A ninth aspect of the invention is that in the fourth aspect of the invention, the magnetic particle integratedly processing apparatus has; a plurality of liquid passages inside of which liquid passes and which are arranged in matrix form, a magnetic force part for exerting and removing a magnetic field onto and from the liquid passages from outside, and a pressure controller for controlling the pressure inside the liquid passages to suck and discharge liquid.

In the ninth aspect of the invention, a magnetic particle integratedly processing apparatus is provided at one of the sets of container working devices. Therefore for magnetic particle suspensions stored in each storage part of a plate-shaped container, rapid and efficient processing can be performed. Hence for the magnetic particles, processing can be performed efficiently at high speed and in various ways.

A tenth aspect of the invention is that in the ninth aspect of the invention, the magnetic force part is able to exert and remove a magnetic force onto and from each nozzle interior, in a stationary condition near an outside of the liquid passages.

In the tenth aspect of the invention, since in the magnetic particle integratedly processing apparatus it is possible to exert and remove a magnetic force onto and from each nozzle interior, in a stationary condition near the outside of the respective liquid passages, then a compact magnetic particle integratedly processing apparatus can be manufactured.

An eleventh aspect of the invention is that that in the tenth aspect of the invention, the magnetic force part is able to exert and remove a magnetic force onto and from each liquid passage interior, in a stationary condition near an outside of the liquid passages, by being able to magnetize and demagnetize an external member of the liquid passages which is set nearby or contacting with an outer surface of each liquid passage.

According to the eleventh aspect of the invention, an effect the same as that described for the tenth aspect of the invention is demonstrated.

A twelve aspect of the invention is that in the eleventh aspect of the invention, the magnetic force part has a magnetic material member formed from a magnetic material provided with a plurality of insertion parts for taking insertion of each liquid passage, and the external member of the liquid passages is a wall part of the insertion parts.

According to the twelfth aspect of the invention, an effect the same as that described for the tenth aspect of the invention is demonstrated.

A thirteenth aspect of the invention is that in the eleventh aspect of the invention, the external member of the liquid passages is made of divided parts which are divided, and each divided part is separated so as to have mutually opposite polarities by magnetizing.

According to the thirteenth aspect of the invention, an effect the same as that described for the tenth aspect of the invention is demonstrated.

A fourteenth aspect of the invention is that in the fourth aspect of the invention, in the dispensing apparatus or the magnetic particle integratedly processing apparatus, a receiving tray is provided so as to be insertable and removable with respect to an area beneath all liquid passages of the dispensing apparatus or the magnetic particle integratedly processing apparatus, for receiving liquid leaking from any of the liquid passages.

In the fourteenth aspect of the invention, because the receiving tray for preventing liquid spill is provided below the bottom end of the liquid passages, reliable processing without cross-contamination can be performed.

A fifteenth aspect of the invention is that in the fourteenth aspect of the invention, an apparatus for stacking the containers or the tip racks stores the containers or tip racks stacked vertically and has; a plurality of storage parts arranged axisymmetrically, a rotation shaft provided on an axis of symmetry line position, a rotation mechanism which rotates about the rotation shaft, and a transfer mechanism for transferring the storage parts in the vertical direction based on the number of containers or tip racks stored in the storage parts.

In the fifteenth aspect of the invention, since the containers or tip racks can be compactly stacked in layers, work space can be decreased and work efficiency increased.

A sixteenth aspect of the invention is that in the fourth aspect of the invention, the apparatus for washing containers has; a plurality of liquid passages capable of insertion into each storage part of the container, an elevating mechanism for elevating the liquid passages, and a sucking and discharging mechanism for sucking and discharging liquid, and the liquid passages have an inner liquid passage and an outer liquid passage, with inner passage passing through the outer passage and being provided protruding slightly from the outer passage at the bottom end, and the sucking and discharging mechanism is controlled so as to discharge or suck cleaning solution from the inner passage and to suck or discharge cleaning solution from the outer passage.

In the sixteenth invention, by sucking and discharging cleaning solution with respect to the containers comprising a plurality of storage parts, the mounted containers can be washed reliably, efficiently and rapidly.

A seventeenth aspect of the invention is that in the fourth aspect of the invention, the constant temperature apparatus has; a mounting part made of thermal conductive material for mounting containers, a Peltier element provided beneath the mounting part and driven by a predetermined direction current, fins provided beneath the Peltier element, and a fan provided beneath the fins, and the mounting part, Peltier element and fins are stored in a accommodating part made of a thermal insulation material and having an opening in a top end and a bottom end, and the fan is installed in the opening in the bottom end of the accommodating part.

According to the seventeenth aspect of the invention, since containers can be heated or cooled by simply mounting the containers, processes can be performed easily without increasing apparatus size.

An eighteenth aspect of the invention is that in the fourth aspect of the invention, the reagent supplying apparatus has;

a plurality of reagent baths which is made of transparent or translucent material for storing reagents, a pipe set communicated with a reagent supply source for supplying reagent to the reagent baths, with tips inserted into the reagent baths so as to be freely inserted and removed, floats provided in the reagent baths, a light emitting part provided outside the reagent baths for irradiating light towards the reagent baths, and a light receiving part provided outside the reagent baths so as to be able to receive light from the reagent baths.

According to the eighteenth aspect of the invention, the reagent supplying apparatus continually detects the liquid level, and in the case where the reagent stored in the reagent bath is insufficient, reagent is supplied so that a constant amount of reagent can always be stored. Also a pipe for supplying reagent is provided in the reagent bath so as to be freely attached and removed. Therefore attachment and removal of the reagent bath is facilitated, and washing or replacement of the reagent bath can be easily performed.

A nineteenth aspect of the invention is a dispensing apparatus with a receiving tray provided so as to be insertable and removable with respect to an area beneath all liquid passages of the dispensing apparatus, for receiving liquid leaking from any of the liquid passages.

According to the nineteenth aspect of the invention, an effect the same as that described for the fourteenth aspect of the invention is demonstrated.

A twentieth aspect of the invention is a magnetic particle integratedly processing apparatus with a receiving tray provided so as to be insertable and removable with respect to an area beneath all liquid passages of the magnetic particle integratedly processing apparatus, for receiving liquid leaking from any of the liquid passages.

According to the twentieth aspect of the invention, an effect the same as that described for the fourteenth aspect of the invention is demonstrated.

A twenty-first aspect of the invention is that the apparatus for stacking the containers or the tip racks is a container stacking apparatus which stores the containers or tip racks stacked vertically and has; a plurality of storage parts arranged axisymmetrically, a rotation shaft provided on an axis of symmetry line position, a rotation mechanism which rotates about the rotation shaft, and a transfer mechanism for transferring the storage parts in the vertical direction based on the number of containers or tip racks stored in the storage parts.

According to the twenty first aspect of the invention, an effect the same as that described for the fifteenth aspect of the invention is demonstrated.

A twenty-second aspect of the invention is a container washing apparatus having; a plurality of liquid passages capable of insertion into each storage part of a container, an elevating mechanism for elevating the liquid passages, and a sucking and discharging mechanism for sucking and discharging liquid, and the liquid passages have an inner liquid passage and an outer liquid passage, with inner passage passing through the outer passage and being provided protruding slightly from the outer passage at the bottom end, and the sucking and discharging mechanism is controlled so as to discharge cleaning solution from the inner passage and to suck cleaning solution from the outer passage.

According to the twenty second aspect of the invention, an effect the same as that described for the sixteenth aspect of the invention is demonstrated.

A twenty-third aspect of the invention is a constant temperature apparatus having; a mounting part made of thermal conductive material for mounting containers, a Peltier element provided beneath the mounting part and driven by a predetermined direction current, fins provided beneath the Peltier element, and a fan provided beneath the fins, and the mounting part, Peltier element and fins are stored in an accommodating part made of a thermal insulation material and having an opening in a top end and a bottom end, and the fan is installed in the opening in the bottom end of the accommodating part.

According to the twenty third aspect of the invention, an effect the same as that described for the seventeenth aspect of the invention is demonstrated.

A twenty-fourth aspect of the invention is a reagent supplying apparatus having; a plurality of reagent baths which is made of transparent or translucent material for storing reagents, a pipe set communicated with a reagent supply source for supplying reagent to the reagent baths, with tips inserted into the reagent bath, so as to be freely inserted and removed, floats provided in the reagent baths, a light emitting part provided outside the reagent bath for irradiating light towards the reagent bath, and a light receiving part provided outside the reagent bath and facing the light emitting part through the reagent bath.

According to the twenty fourth aspect of the invention, an effect the same as that described for the eighteenth aspect of the invention is demonstrated.

A twenty-fifth aspect of the of the invention has; a turntable capable of mounting a specified quantity of plate-shaped containers each having a specified quantity of storage parts arranged in matrix form, or a specified quantity of tip racks each storing a specified quantity of pipette tips, and simultaneously transferring in both a forward and reverse direction along a circular route, a plurality of container working devices arranged in an area outside of the route of the turntable and along the route direction, for performing various kinds of operations on the containers mounted on the turntable or the contents thereof or containers mounted at predetermined positions outside of the turntable or the contents thereof, a robot provided in an inside area surrounded by the route, having a holding part capable of holding the containers or the tip racks, and an arm connected to the holding part and capable of moving the holding part between arbitrary positions inside an area including mounting positions of the containers on the turntable and on the sets of container working devices, and a control part for performing transfer of the turntable, operation of the sets of container working devices, and control of the robot; and the plurality of sets of container working devices are; a dispensing apparatus, a magnetic particle integratedly processing apparatus, a constant temperature apparatus for cooling or heating, a stacking apparatus for stacking the containers or the tip racks, a reagent supplying apparatus, a container washing apparatus, a nozzle tip washing apparatus and a measuring apparatus for measuring the contents of the containers.

Here there are two types of "tip rack", one for arranging the tips in matrix form corresponding to the magnetic particle integratedly processing apparatus, and one for arranging a number of tips equivalent to the number of nozzles corresponding to the dispensing apparatus. "Contents in a container" includes for example genetic material such as DNA, biopolymers such as proteins, microorganism such as cells and bacteria, biomedical tissue of organisms, and so on.

According to the twenty fifth aspect of the invention, an effect the same as that described for the first aspect of the invention is demonstrated.

BEST MODE FOR CARRYING OUT THE INVENTION

A container transfer and processing system according to an embodiment of the present invention will be explained with reference to the drawings. This embodiment does not limit the present invention unless particularly specified.

Figure 1:
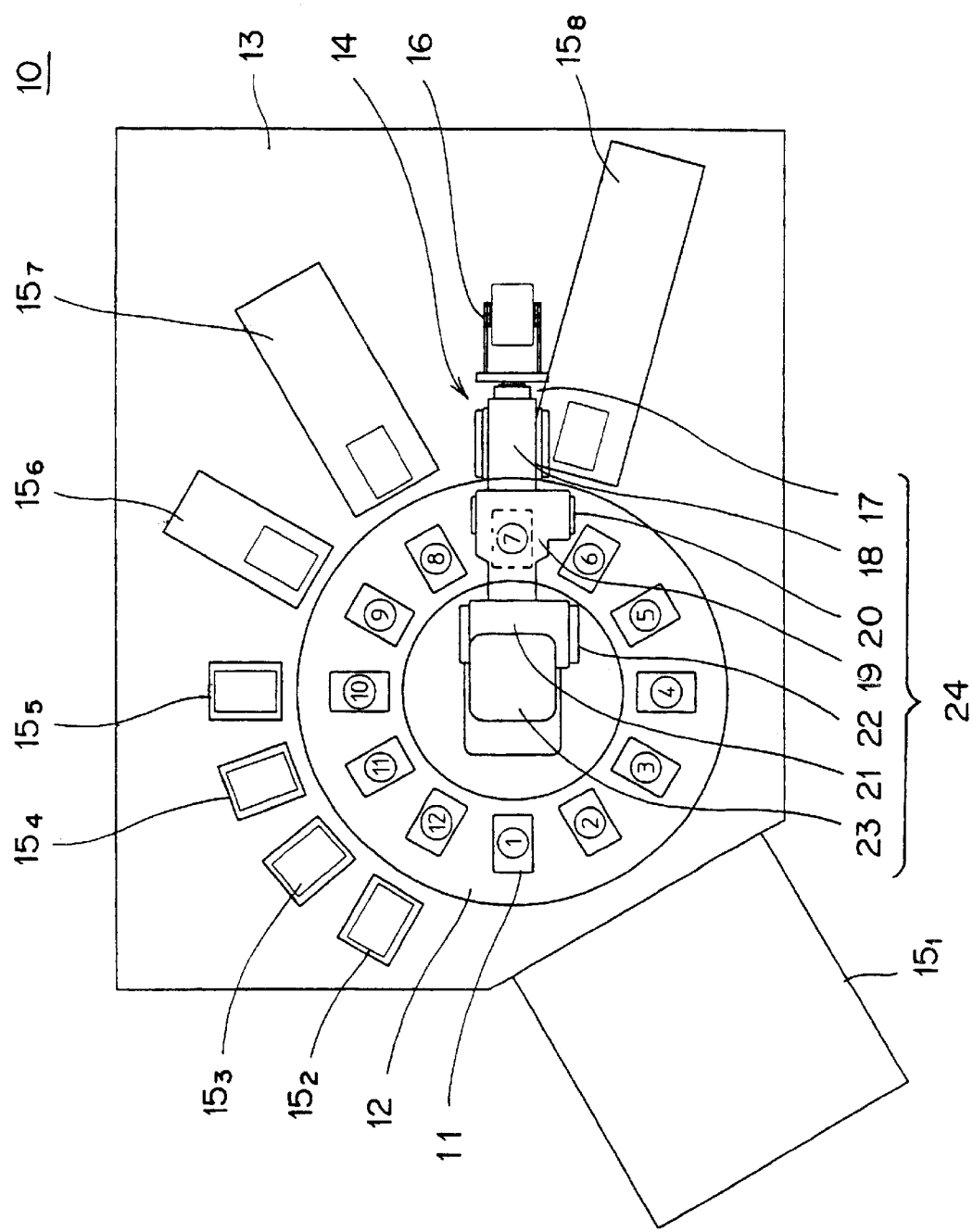
FIG. 1 is a drawing illustrating the principle of a container transfer and processing system according to an embodiment of the present invention.

FIG. 1 illustrates the principle of a container transfer and processing system 10 according to this embodiment. As shown in the figure, the container transfer and processing system 10, has for example, for transferring plate-shaped containers 11 each having for example 96 (8×12) storage parts arranged in matrix form, or tip racks in which are stored similarly arranged pipette tips, a turntable 12 as a simultaneous transfer device for simultaneous transfer of the containers, carrying a maximum of 12 items and provided so as to be rotatable in both the forward and reverse directions along a closed circular shape closed route. The inner bottom of the storage parts of the container 11 are formed for example as a round bottom so that when a tip is inserted, the tip can suck or discharge while in contact with the bottom.

In an area outside of the route of the turntable 12, there is provided a base table 13, and inside the area of the turntable 12 is installed a rotation shaft set concentric with the center of rotation of the turntable 12, and which has a robot 14 provided so as to be rotatable at least ±360°, for individually transferring the containers 11 or the tip racks one by one.

This container transfer and processing system 10 is provided with; an operation apparatus (not shown in the figures) comprising; a keyboard to input or designate processing or operation contents by an operator, a mouse, a touch panel, a floppy disk driver, an input part such as a communication apparatus, a display part such as a CRT or LCD, a printing device or communication device, and an output part comprising a floppy disk driver or the like, and a control section (not shown in the figures) comprising a CPU or the like for analyzing instruction contents, and instructing control to the turntable.

In the outside area of the turntable 12 including the base table 13 there is arranged along the periphery of the turntable 12, a plurality of container working devices $15_1$ to $15_8$, which perform a variety of operations.

The robot 14 is able to transfer the plate-shaped containers 11 or tip racks 37 between arbitrary positions inside an area including the mounting position of the containers on the turntable 12 and on the sets of container working devices $15_1$ to $15_8$. The robot 14 has a hand part 16 as a holding part capable of holding the containers 11 or tip racks, and an arm 24 which is connected to the hand part 16 and which can transfer the hand part 16 within the area including the mounting positions of the containers 11 or tip racks on the turntable 12 and on the sets of container working devices $15_1$ to $15_8$.

The arm 24 is an articulated robot which has; a first arm 18 for rotatably connecting to the hand part 16 through a junction 17, a second arm 19 for rotatably connecting to the first arm 18 through a joint 20, and a base 21 for rotatably connecting to the second arm 19 through a joint 22. The base 21 of the robot 14 has a rotation shaft 23 concentric with a center of rotation of the turntable 12. The arm 24 is controlled so as not to collide with the sets of container working devices $15_1$ to $15_8$.

Figure 2:
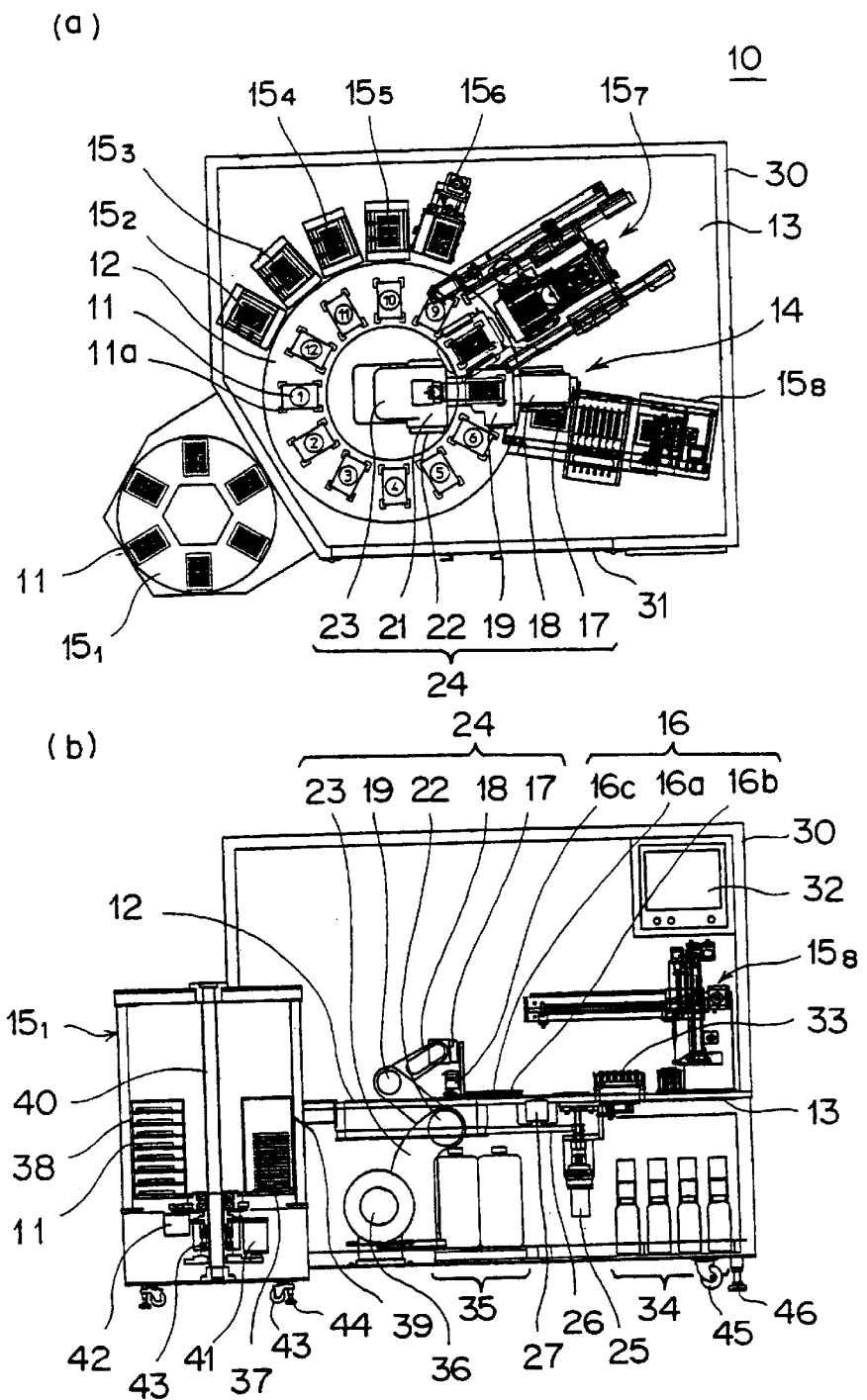
FIG. 2 is a detailed drawing of a container transfer and processing system according to the embodiment of the present invention.

FIG. 2 shows all sets of container working devices 10 in more detail.

As it is shown in FIG. 2(a), the set of container working devices $15_1$ to $15_8$ are, for example; a stacking apparatus $15_1$ for stacking the containers 11 and tip racks 37 outside the transfer route, constant temperature apparatus $15_2$ to $15_5$ for heating or cooling the containers 11 outside the transfer route, a container washing apparatus $15_6$ for washing each storage part of the container 11 outside the transfer route, a magnetic particle integratedly processing apparatus $15_7$ for performing various kinds of processing on suspensions containing magnetic particles which are stored in the containers 11 inside the transfer route, or attaching pipette tips onto or removing them from the tip racks 37, a multi row dispensing apparatus $15_8$ for performing dispensing or the like with respect to the containers 11 outside the transferring route, and a reagent supply apparatus for supplying various kinds of reagents to the containers 11 outside the transferring route.

The containers 11 to be processed by the container transfer and processing apparatus, are secured in position on the turntable 12 so as not to move by providing four fasteners 11a for each container 11 at each corner of the container 11.

A holding part 16 of the robot 14, as shown in FIG. 2(b) has an L-shape member 16a, and a clamping part 16b provided beneath the L-shape part 16a and a motor 16c for driving the clamping part 16b, which are connected to the arm 18 through the joint 17.

The turntable 12 is rotation driven by a motor 25 through a timing belt 26. Bearings 27 are provided between the turntable 12 and the base table 13.

The sets of container working devices $15_2$ to $15_8$, excluding the turntable 12, the base table 13, the robot 14 and the container stacking apparatus $15_1$, are accommodated in a sealed storage chamber 30. As a result, it is possible to prevent influence from outside on the processing material, or dispersion of material which might have a harmful effect on humans or the environment, to the open air. Moreover, a door 31 which can be freely opened or closed is provided in the storage chamber 30, and a display apparatus 32 is provided on the storage chamber 30, for displaying process result of the container transfer and processing apparatus 10, aspects of the processing, processing settings, and so on. Furthermore inside the storage chamber 30 there may be provided exhaust ports with filters (not shown in the figures) for exhausting gas accumulated there inside.

In FIG. 2(b), beneath the turntable 12 and the base table 13 there is provided; reagent bottles 34 for storing reagent for supply to the reagent supplying apparatus 33, in which is stored reagent dispensed by the dispensing apparatus $15_8$, bottles 35 for storing cleaning solution for supply to the washing apparatus $15_6$ and a blower 36 for supplying air to the washing apparatus $15_6$ and the like.

The container stacking apparatus $15_1$ has storage parts 38 and 39 for respectively storing the plate-shaped containers 11 or tip racks 37 by stacking and arranging axisymmetrically. Moreover, on symmetrical axes therewith there is provided; a rotation shaft 40, a motor 41 which rotates the respective storage parts 38 and 39 about the rotation shaft 40, and a motor 42 for moving the respective storage parts 38 and 39 up and down. Reference symbol 43 denotes a bearing. The outside container stacking apparatus $15_6$ and the storage chamber 30 may be made movable by providing casters 43 and 45 and legs 44 and 46.

Next is a description of another sets of container working devices $15_2$ to $15_8$ according to this embodiment with reference to the drawings. At first is a description of a magnetic particle integratedly processing apparatus $15_7$, with reference to FIG. 3.

This magnetic particle integratedly processing apparatus $15_7$ has; pipette tips 50 of 8 rows×12 columns arranged in matrix form (only the 12 columns are shown in the figure), nozzles 51 inserted removably into the tips 50 (there are 8 rows×12 columns, but only one row is shown in the figure for simplicity), cylinders 52 communicated with the nozzles 51 (there are 8 rows×12 columns, but only one row is shown in the figure for simplicity), and pistons 53 arranged in matrix form which are stored in each of the cylinders 52 so as to be movable up and down (there are 8 rows×12 columns, but only one row is shown in the figure for simplicity). These pistons 53 are attached at the top to a moving part 54. The moving part 54 is provided so as to be slideable relative to a syringe base plate 57, via a guide part 55, along a vertically laid rail 56.

The moving part 54 is rotatably connected to the bottom end of a ball screw 58, and the ball screw 58 is threaded into a nut 59. The nut 59 is rotationally driven by a motor 60 through a timing belt 61. The motor 60, the cylinders 52, the nozzles 51 and the pipette tips 50 are fixed to the syringe base plate 57.

The syringe base plate 57, and the nozzles 51, the cylinders 52 and the pipette tips 50 fixed thereto are moved up and down by a vertical movement mechanism 62. The vertical movement mechanism 62 has; a rail 64 for guiding a guide 63 which is provided fixed to the syringe base plate 57, a nut 65 connected to the guide 63 of the syringe base plate 57, a ball screw 66 threaded into the nut 65, and a motor 68 for vertically moving the nut 65 by rotational driving the ball screw 66 through a coupling 67. The bottom end of the ball screw 66 is rotatably supported by a bearing 64.

Furthermore, the vertical movement mechanism 62 is supported so as to be movable in the radial direction by a rail member 70 provided along the radial direction of the turntable 12. The rail member 70 is fixed to the base table 13 by a support 71.

A receiving tray 72 for receiving leaked liquid from the pipette tips 50 is provided at the bottom side of the vertical movement mechanism 62, so as to be inserted into and removed from the area beneath the tips 50 in the figure. Reference symbol 73 denotes a motor for moving the receiving tray 72 for insertion and withdrawal. The receiving tray 72 is made from flexible material, and at the backward position is bent along the curved surface 74 in FIG. 3(b).

A magnetic force part 75 is provided beneath the receiving tray 72 at the bottom end of the vertical movement mechanism 62. The magnetic force part 75 has a magnetic source 78 which is positionally adjustable transversely in the figure with respect to the bottom end part of the vertical movement mechanism 62, via a guiding part 76 and a rail 77 for guiding the guiding part 76, and a magnetic substance 79 magnetically connected to the magnetic source 78 and having a plurality of insertion parts into which the matrix shape arranged tips 50 can be inserted.

Figure 3:
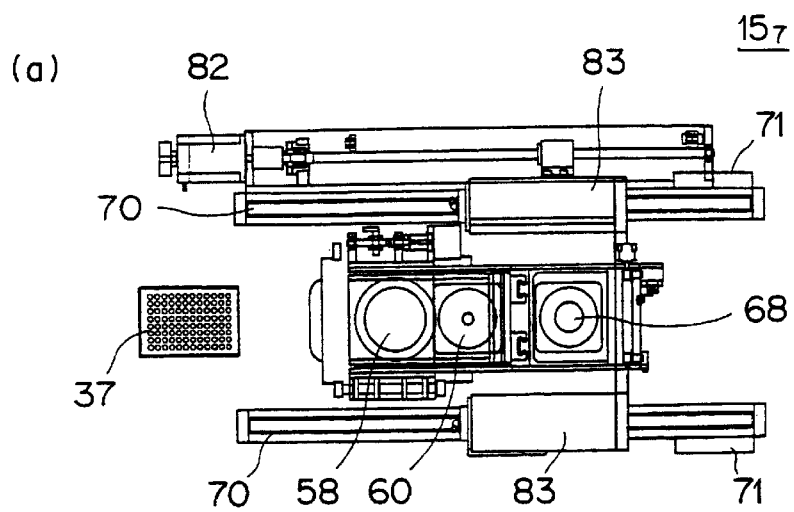
FIG. 3 is a front view and a plan view of a magnetic particle integratedly processing apparatus according to an embodiment of the present invention.
Figure 3:
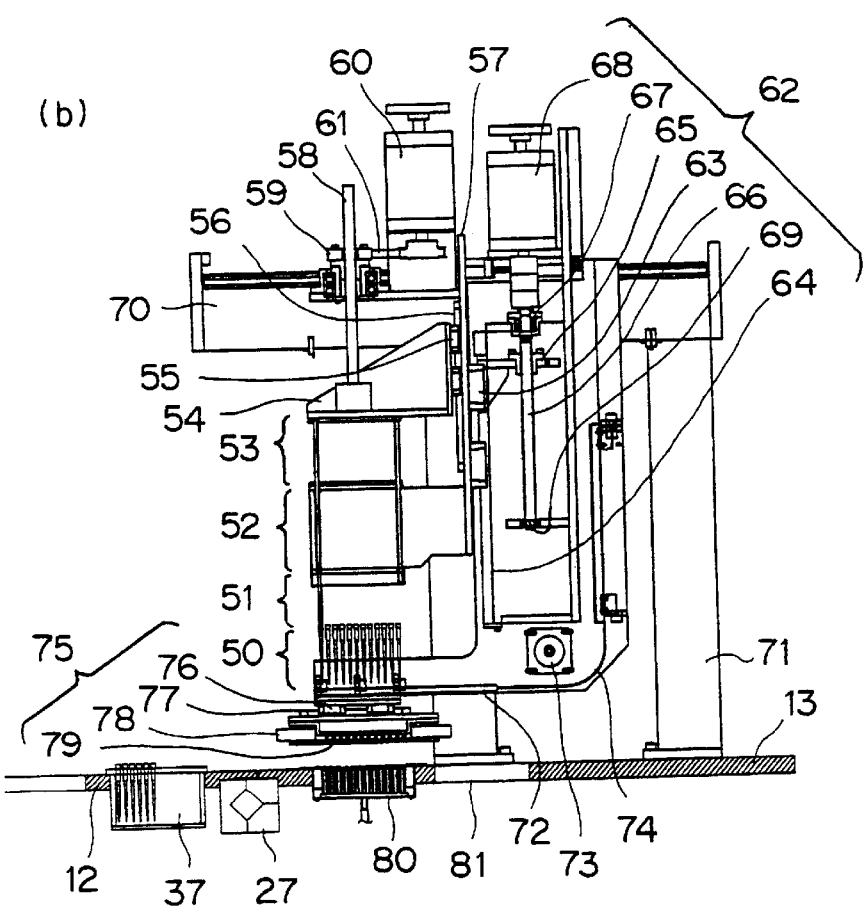

Reference symbol 80 in the FIG. 3 denotes a washing apparatus for washing tips or nozzles, while reference symbol 81 denotes an opening for removal and dumping of the tips. Furthermore, reference symbol 82 denotes a motor for moving a part including the vertical movement mechanism 62 in a radial direction of the turntable 12, and reference symbol 83 denotes a support for slidably supporting a part including the vertical movement mechanism 62 on the rail member 70.

Figure 4:
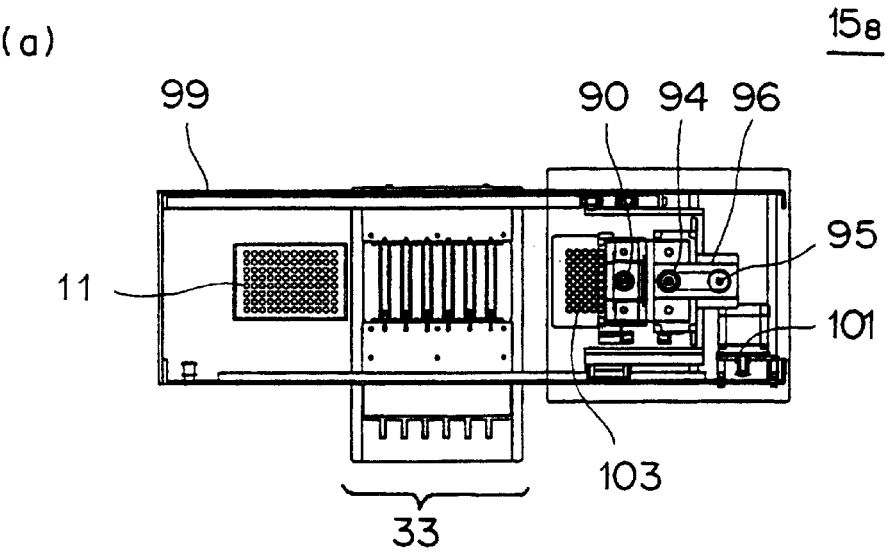
FIG. 4 is a front view and a plan view of a dispensing apparatus according to an embodiment of the present invention.
Figure 4:
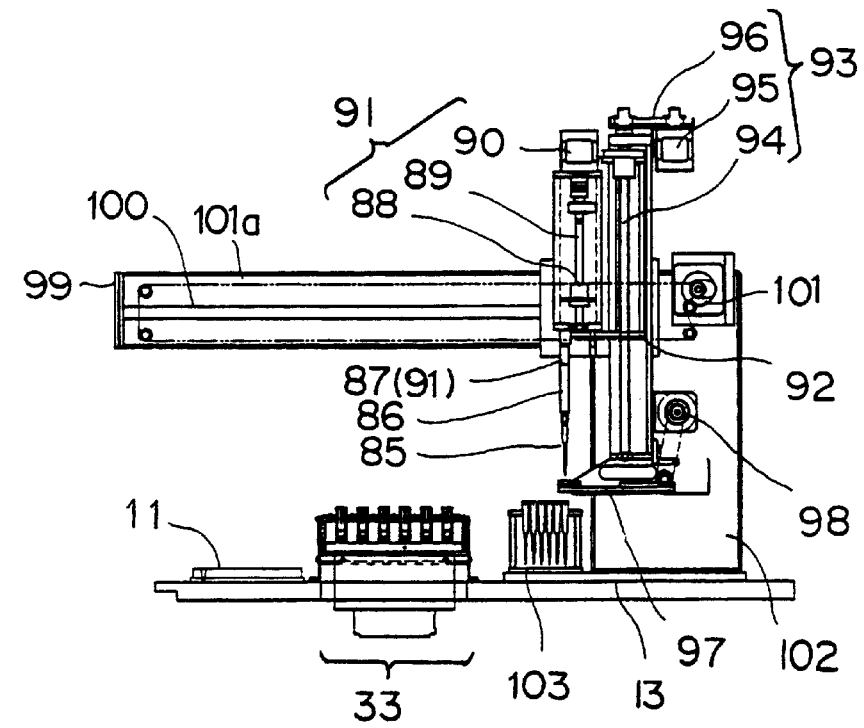

Next is a description of the dispensing apparatus $15_8$ based on FIG. 4.

The dispensing apparatus $15_8$ has a plurality of, for example 8, sets of nozzles.

The dispensing apparatus $15_8$ has tips 85 having tip ends which can be inserted into the storage parts of the containers 11, cylinders 86 having a nozzles onto which the tips 85 can be attached and removed freely, pistons 87 slidably accommodated in the cylinders 86 for sucking and discharging by moving vertically, a nut 88 connected to the pistons 87, a ball screw 89 threaded into the nut 88, and a motor 90 for rotating and driving the ball screw 89.

The pistons 87, the nut 88, the ball screw 89 and the motor 90 constitute a sucking and discharging mechanism 91. All of the sucking and discharging mechanism 91, the pipette tips 85, and the cylinders 86 with nozzles attached are fixed to a support 92. Through the support 92, the pipette tips 85 and other parts, are supported so as to be movable up and down by a vertical movement mechanism 93.

The vertical movement mechanism 93 has a ball screw 94 which is threaded into a nut (not shown in the figure) provided on the support 92, and the ball screw 94 is rotated and driven by a motor 95 through a timing belt 96.

At the bottom end of the vertical movement mechanism 93, there is provided a receiving tray 97 for receiving leaked liquid from the tip end of the tips 85, provided so as to be inserted into and withdrawn from the area beneath the tips 85, and a motor 98 for driving for inserting and withdrawing the receiving tray 97.

The vertical movement mechanism 93, the sucking and discharging mechanism 91 and the pipette tips 85 and so on, are provided so as to be movable by a motor 101 and a belt 101a in the back and forth direction along a rail 100 provided on an arm 99. The whole mechanism including the arm 99 is supported by a base 102 and fixed on a base table 13.

Within an area in which the tips 85 of the dispensing apparatus $15_8$ are movable back and forth, there is provided; a plate 11 provided with a plurality of storage parts, a reagent supplying part 33 for supplying reagent, and a tip rack 103 for holding tips which are to be attached to the cylinder 86 fitted with nozzles, or tips which have been removed therefrom. This tip rack 103 may also be transferred by the turntable 12. Regarding the tip racks 37 and 103, in order to prevent cross-contamination between adjacent tips when the used tips are fitted for recycling, a cover for separating each tip may be provided beneath the tip rack 103. The cover may be for example one where holes for insertion of the tips are provided in polystyrene foam.

Figure 5:
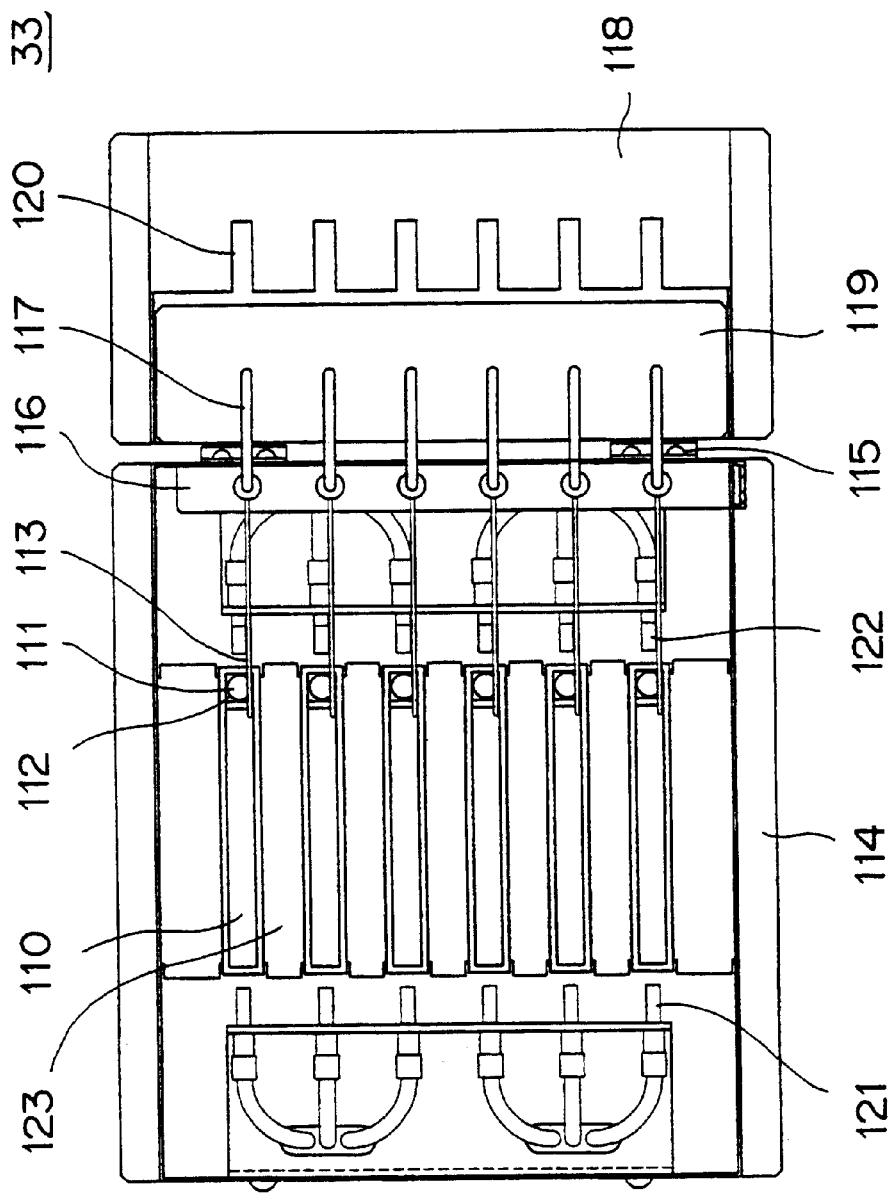
FIG. 5 is a plan view of a reagent supplying apparatus according to an embodiment of the present invention.

FIG. 5 shows details of the reagent supplying part 33.

The reagent supplying part 33 has reagent baths 110 for storing reagents, provided in parallel in a number corresponding to the number of nozzles of the dispensing apparatus $15_8$, and made from transparent or semitransparent material. In each reagent bath 110 a spherical float 111 which floats on the liquid surface of the stored reagent is provided so as to be movable up and down at one end 112 inside the reagent bath 110.

In each reagent bath 110, a tip end of a small diameter metal pipe 113 for supplying reagent is removably inserted from above an open part of each reagent bath 110. Each of these pipes 113 is attached to a holding part 116, which is open and closably connected to a frame 114 of the reagent supplying part 33 by a hinge 115.

The pipe 113 is connected to a flexible pipe 117 which is communicated with a tank for storing reagents. The flexible pipe 117 is attached to a flexible pipe connecting part 119 of a pipe laying part 118. The pipe laying part 118 is for laying the pipes 113 in the case where the holding part 116 is opened and the pipes 113 are removed from the reagent bath 110. Reference symbol 120 denotes notches in which the pipes 113 are inserted and laid.

Furthermore, in the reagent supplying part 33, a light emitting diode (photodetector) 121 and a photodetector (light emitting diode) 122 are provided such that the optical axis thereof passes through a predetermined position region of each reagent bath 110 which is made from transparent or semitransparent material. In the case where a predetermined amount of reagent is stored inside the reagent bath 110, the float 111 comes within the predetermined position region and light from the light emitting diode 121 (122) is obstructed by the float 111 so that the amount of light received by the photodetector 122 (or 121) is less than a certain amount.

On the other hand, in the case where the reagent is reduced to less than a predetermined amount, the float 111 falls below the predetermined position region and when the light interception device 122 (121) receives almost all the light amount from the light emitting diode 121 (122), the lack of reagent in a reagent bath 110 is detected. Therefore it is possible to control so as to always supply a certain amount of reagent to inside the reagent bath 110.

Reference symbol 123 denotes an aluminum block for reagent cooling.

Figure 6:
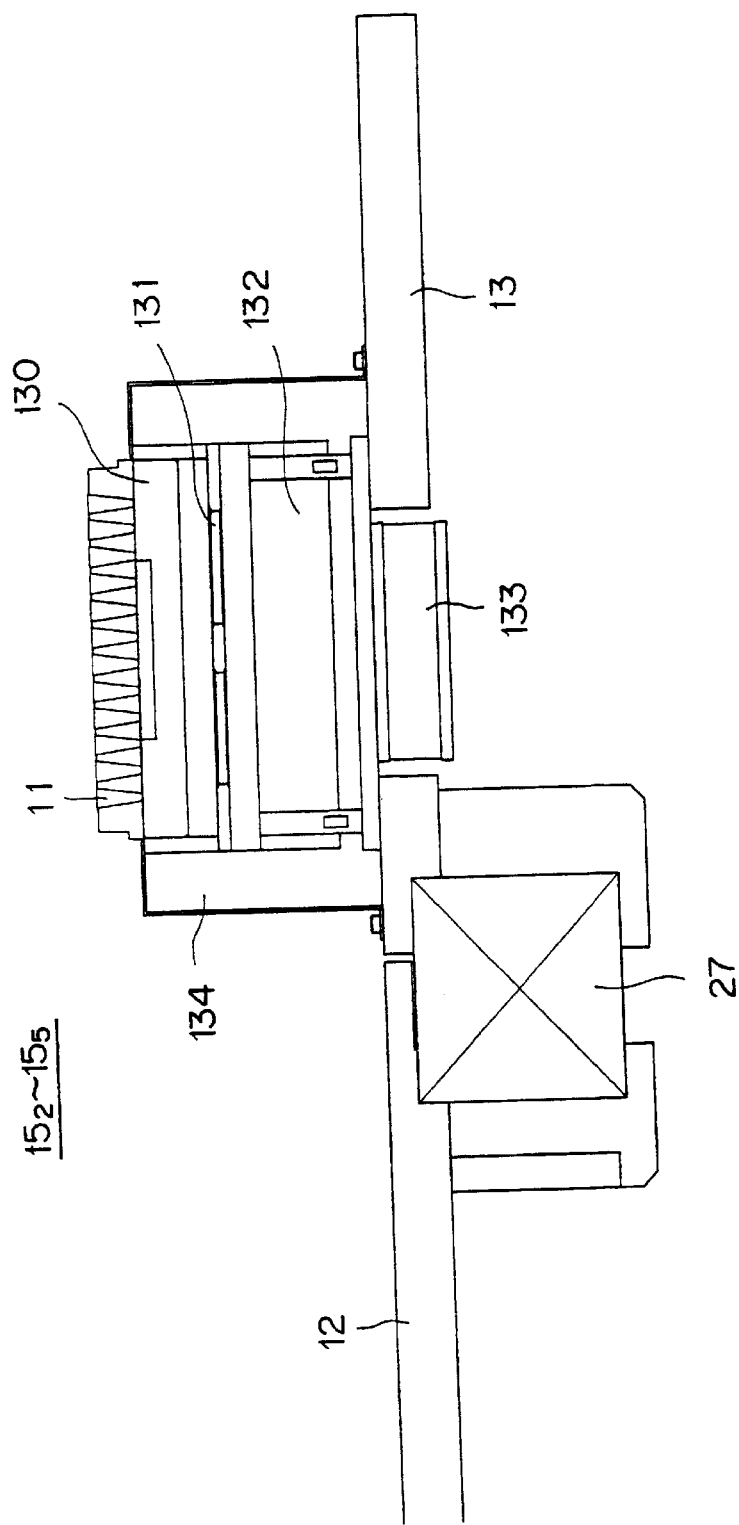
FIG. 6 is a view showing a constant temperature apparatus according to an embodiment of the present invention.

FIG. 6 shows the constant temperature apparatus $15_2$ to $15_5$ for heating or cooling.

The constant temperature apparatus $15_2$ to $15_5$ have thermoconductive material 130 for mounting a container 11 on top, and a Peltier element 131 which becomes a heating source or a cooling source depending on the direction of the electric current. When used for heating, the electric current flows so that heat is generated at the upper surface of the Peltier element 131, and the lower surface is cooled, while when used for cooling, conversely the electric current flows so that the upper surface is cooled and the lower surface is heated.

Fins 132 for radiant heating or radiant cooling are provided beneath the Peltier element 131, and a fan 133 for introducing outside air to the fins 132 is provided beneath the fins 132. The thermoconductive material 130, the Peltier element 131 and so on are accommodated in a box 134 which is made from thermal insulation material.

Figure 7:
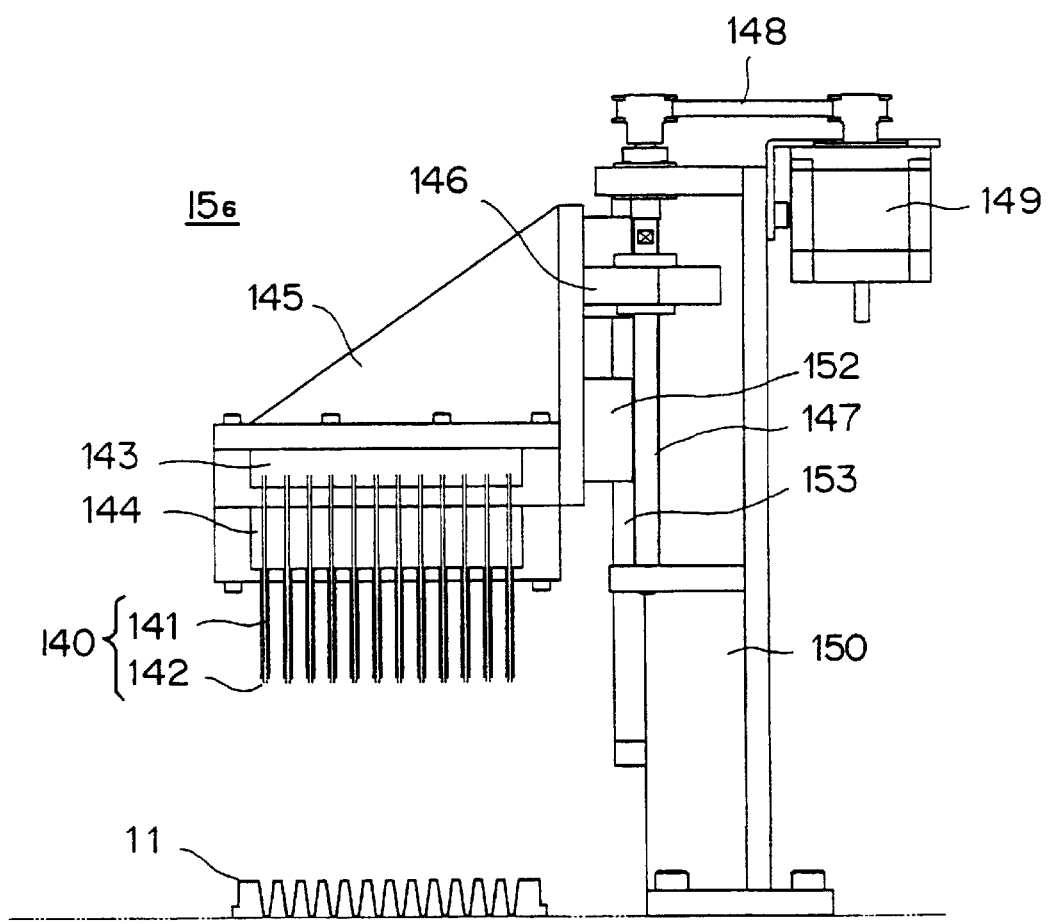
FIG. 7 is a view showing a container washing apparatus according to an embodiment of the present invention.

FIG. 7 shows a plate-shaped container washing apparatus $15_6$. The plate-shaped container washing apparatus $15_6$ is an apparatus for washing mounted plate-shaped containers 11, and has twin pipes 140 arranged in matrix form for inserting into the storage parts of the plate-shaped container 11. The twin pipes 140 comprises an outer pipe 141 and an inner pipe 142 which passes through the outer pipe 141.

The inner pipe 142 is for spraying or discharging cleaning solution to each storage part, and is communicated with the aforementioned cleaning solution bottles 35 through a cleaning solution holding part 143 for temporarily holding cleaning solution prior to discharging. The outer pipe 141 is for sucking cleaning solution which has been sprayed or discharged to each storage part, and is communicated with a cleaning solution discharge part 144 and sucks or discharges using the aforementioned blower 36. Here cleaning solution includes, for instance, distilled water.

The twin pipes 140, the cleaning solution holding part 143 and the cleaning solution discharge part 144 are attached and fixed to an attachment part 145. The attachment part 145 is connected to a nut 146. The nut 146 is threaded with a ball screw 147, and by rotation of the ball screw 147, the nut 146 and the attachment part 145, and thus the twin pipes 140 are moved up and down. The ball screw 147 is rotated and driven by a motor 149 through a timing belt 148. These vertical movement mechanisms are provided secured to a base table 13 by a stand 150.

A guide 152 is provided on the attachment part 145, and by moving the guide 152 up and down guided by a rail 153, the attachment part 145 is stably moved up and down. According to this apparatus, by moving the twin pipes 140 up and down, a sucking and discharge action can be performed at various positions in the vertical direction inside the storage part, thus enabling reliable washing. Moreover, according to this apparatus, the discharge volume of cleaning solution can be variably set, and can thus be made to correspond to containers having various capacities.

Figure 8:
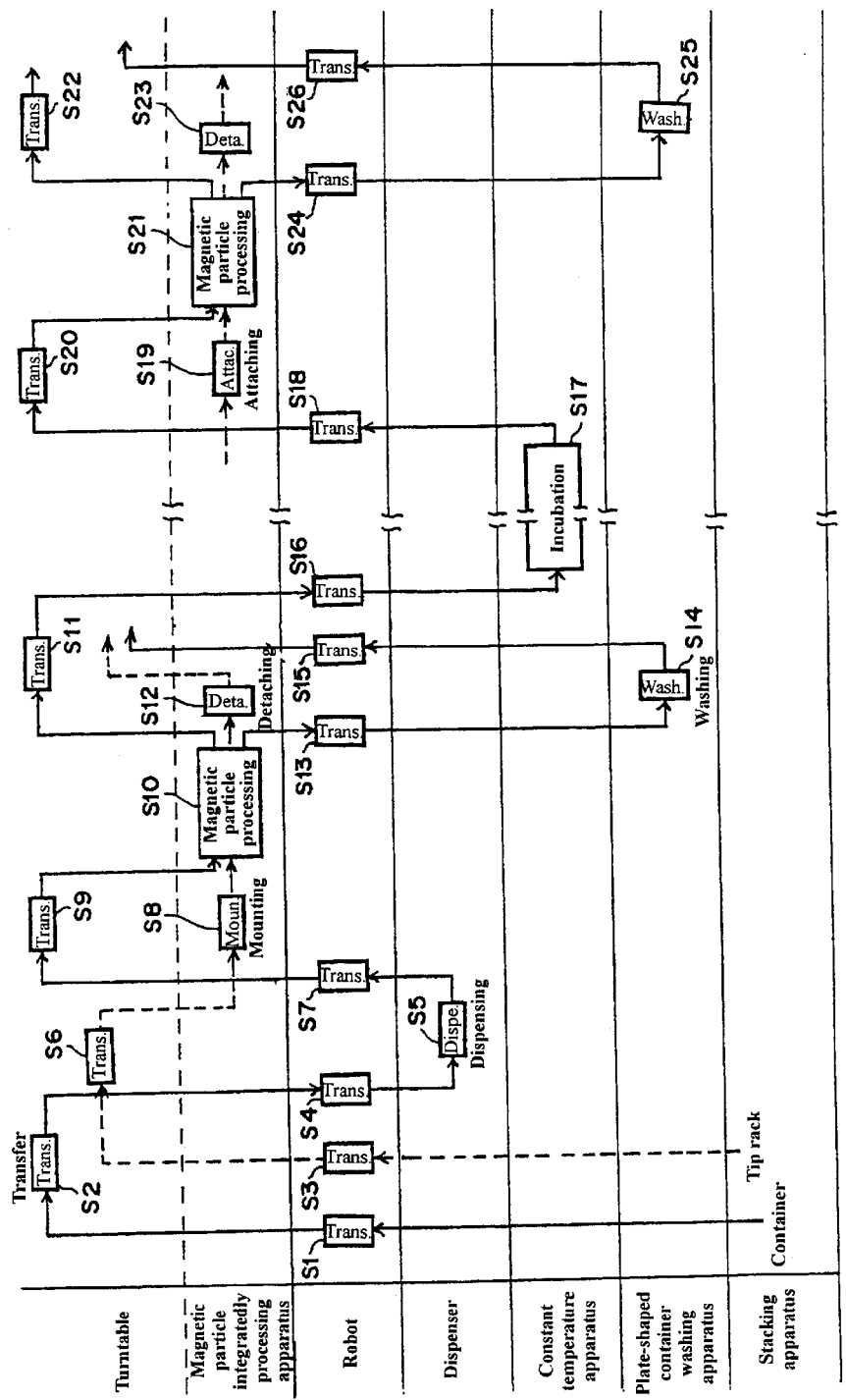
FIG. 8 is a process flow chart of the container transfer and processing apparatus according to the embodiment of the present invention.

The operation of the container transfer and processing system 10 according to the embodiment will now be explained based on FIG. 8.

When an operator specifies a process by inputting the process content using the aforementioned operation apparatus, the control part recognizes the process content. Then as shown in FIG. 8, in step S1, the robot 14 takes out a container 11 in which samples such as specimens are stored in each storage part, from the stacking apparatus $15_1$, and transfers this, and mounts it on the turntable 12.

Then the turntable 12, in step S2, transfers the container 11 to the vicinity of the dispensing apparatus $15_8$ on the turntable 12, and in step 4, this is transferred to a working area of the dispensing apparatus $15_8$, by the robot 14. In step 5, a reagent and a magnetic particle suspension, necessary for the aforementioned process, are dispensed in the necessary quantity to each storage part of the container 11 by the dispensing apparatus $15_8$. A capture material necessary for capturing a target material, is coated onto the magnetic particle.

In the meantirne, the robot 14 in step S3, takes out tip racks 37 in which the tips 50 are arranged, from the aforementioned container stacking apparatus $15_1$, and transfers these, and mounts them onto the turntable 12. The tip racks 37 are transferred to the vicinity of the magnetic particle integratedly processing apparatus $15_7$ by the turntable 12, and then in step S8, on the route, these are attached all together to the nozzles 51 by lowering the nozzles 51 of the magnetic particle integratedly processing apparatus $15_7$ onto the tip racks 37.

On the other hand in step S7, a container 11 which has been subjected to the dispensing process is transferred by the robot 14 and mounted onto the turntable 12, and in step S9 this is transferred to the vicinity of the magnetic particle integratedly processing apparatus $15_7$ by the turntable 12. Then in step S10 the pipette tips 50 which are attached to the nozzles 51 of the magnetic particle integratedly processing apparatus $15_7$, are inserted into the container 11 to perform the process for the magnetic particles. This process includes processes such as suction, discharge, mixing, separation, dissociation of the target material, and re-suspension.

Once the process is finished, in step S11, the dissociated target material is stored into a container 11 together with a necessary reagent and transferred by mounting onto the turntable 12. Moreover, in the case of recycling the used container 11, in step S13, the container 11 is transferred to the aforementioned plate-shaped container washing apparatus $15_6$ by the robot 14 (the turntable 12 may also be used), and in step S14 the washing process is performed.

The washed container 11, in step S15, is transferred by the robot, and mounted on the turntable 12. Furthermore, the used pipette tips 50, which are attached to the magnetic particle integratedly processing apparatus $15_7$, depending on necessity in the magnetic particle processing of step S10, are washed while attached to the nozzles by the washing apparatus 80 shown in FIG. 3(b). In step S12, the used unnecessary tips 50 may be detached and stored in the tip rack 37, and transferred to the vicinity of the stacking apparatus $15_1$ on the turntable 12, and then stored in the stacking apparatus $15_1$ by the robot 14.

On the other hand in step S11, the container 11, in which the target material and necessary reagent are stored, is transferred to the vicinity of one of the constant temperature apparatus $15_2$ to $15_5$. Then in step S16 this is mounted onto one of constant temperature apparatus $15_2$ to $15_5$ by the robot 14, and in step S17 incubation is performed. When the comparatively long period of incubation finishes, in step 18 the robot 14 takes out the container 11 from one of the constant temperature apparatus $15_2$ to $15_5$, and transfers the container 11 to the turntable 12 and mounts it thereon.

In step S19, the magnetic particle integratedly processing apparatus $15_7$, attaches new pipette tips 50 which are arranged in the tip rack 37 mounted on the turntable 12, to the nozzles 51, and in step S21, performs processing of the magnetic particles. Here afresh, the magnetic particle suspension is mixed in the container 11, the processed target material is captured on the magnetic particles, and after eliminating the residual liquid, the target material is dissociated, and re-suspended and stored into a new container 11. Then in step S22, the new container in which the processed target material is stored, is transferred using the turntable 12, and then stored in the stacking apparatus $15_1$ using the robot 14.

Moreover, the used tips 50 are washed by the washing apparatus 80, and then removed in step S23, and eventually returned to the stacking apparatus $15_1$. The used container 11, in step S24, is transferred to the plate-shaped container washing apparatus $15_6$ by the robot 14 (the turntable 12 can also be used). Then after washing in step S25, this is again transferred in step S26, to the turntable 12 by the robot 14, and eventually transferred to the stacking apparatus $15_1$ using the robot 14 and stored.

According to this embodiment, regarding transfer by the robot 14, since transfer is performed when a container 11 is brought close to each set of container working devices by the turntable 12, the load on the robot 14 is reduced, and effectively, the overall processing speed and efficiency is increased.

The above steps illustrate an example of the flow of processes where, to simplify explanation, attention is given only to processing using one target material. However, it is possible to process efficiently and rapidly by processing in continuation with other processes, or by processing in parallel during the processing in step S17, step S10 or step S21 in FIG. 8.

Figure 9:
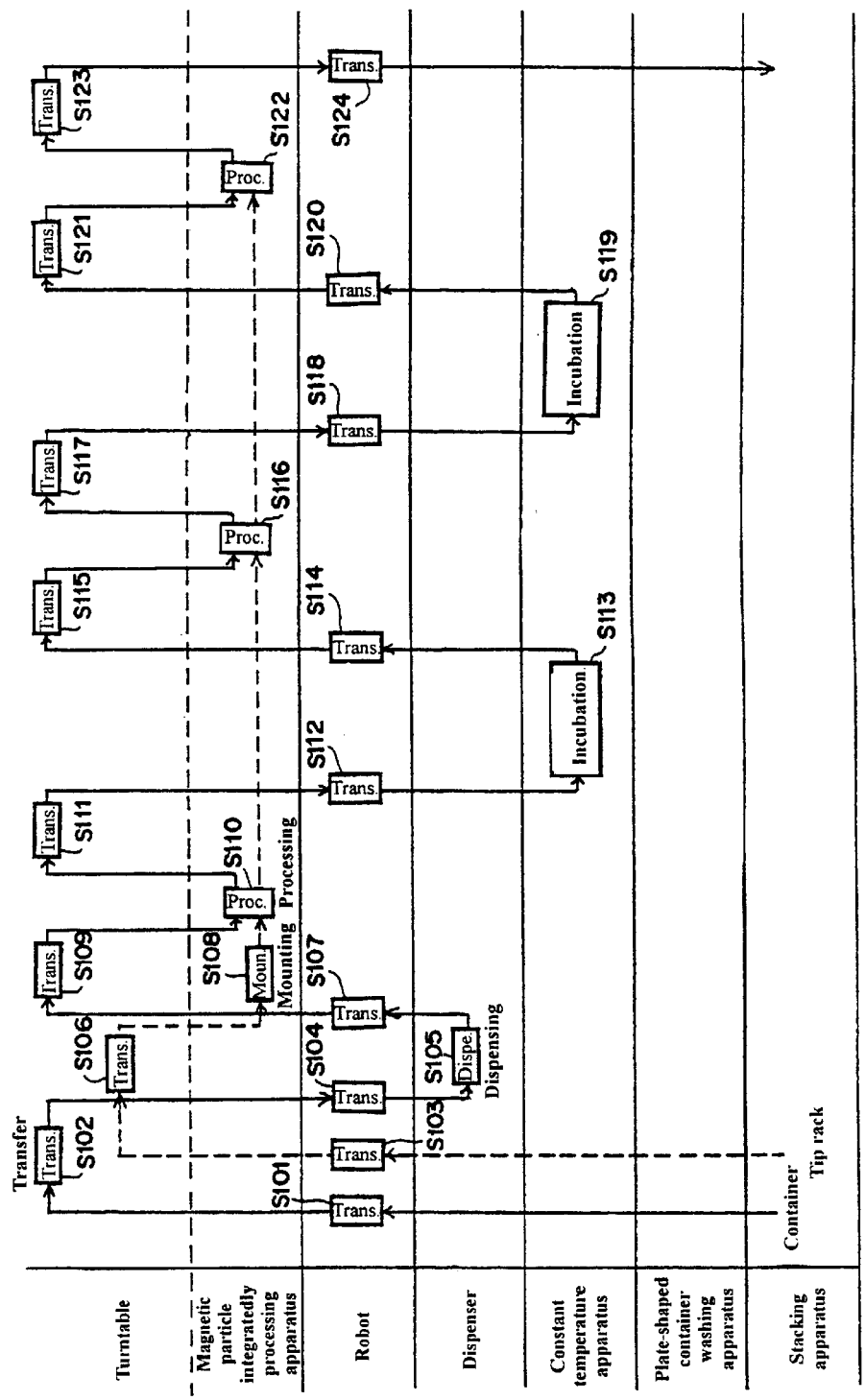
FIG. 9 is another process flow chart of the container transfer and processing apparatus according to the embodiment of the present invention.

An example of application to a dye terminator-clean up process is shown based on FIG. 9.

When an operator specifies a process by inputting the process content using the aforementioned operation apparatus, the control part recognizes the process content. Then in step S101, the robot 14 takes out a plate-shaped container 11 having five sets of 96 storage parts, from the stacking apparatus $15_1$, and sequentially transfers and mounts this on the turntable 12.

In step S102, the container 11 is transferred to the vicinity of the dispensing apparatus $15_8$, and in step S104 this is sequentially transferred by the robot 14 to a working area of the dispensing apparatus $15_8$.

In step S105, by means of the dispensing apparatus $15_8$, sequentially the samples are dispensed into the first container, the magnetic particle suspension is dispensed into the second container, the binding buffer solution is dispensed into the third container, 70% ethanol solution is dispensed into the fourth container, and loading buffer solution is dispensed into the fifth container. A necessary capture material is coated onto the magnetic particle.

Meanwhile, in step S103, the robot 14 takes out a tip rack 37 with 96 tips 50 arranged in matrix form, from the stacking apparatus $15_1$, and transfers this and mounts it onto the turntable 12. The tip rack 37 is then transferred to the magnetic particle integratedly processing apparatus $15_7$ by the turntable 12. In step S108, on the route, each nozzle 51 of the magnetic particle integratedly processing apparatus $15_7$ is lowered to the tip rack 37 to attach the pipette tips 50 all together.

On the other hand in step S107, the 5 piece containers 11 which have been subjected to the dispensing process are sequentially transferred by the robot 11 and mounted on the turntable 12. Then in step S109, these are transferred to the magnetic particle integratedly processing apparatus $15_7$ by the turntable 12. In step S110 the 96 pipette tips 50 arranged in matrix form and attached to the nozzles 51 of the magnetic particle integratedly processing apparatus $15_7$, are at first inserted into each storage part of the first container to suck the sample.

The pipette tips 50 which have sucked the sample are once raised, and when the second container is transferred to directly beneath the pipette tips 50, these are inserted into each storage part of the second container to discharge the sample into the magnetic particle suspension and then suck the mixed liquid. The pipette tips 50, which have sucked the mixed liquid are again raised, and when the third container is transferred to directly beneath the pipette tips 50, the mixed liquid is discharged into the binding buffer solution.

In step S112, the third container is transferred by the turntable 12 to nearby one of the constant temperature apparatus $15_2$ to $15_5$ which provides a temperature of 15° C. Then in step S114, the third container is mounted on one of the constant temperature apparatus $15_2$ to $15_5$ by the robot 14, and in step S113, this is left sitting for example for five minutes.

After the five minutes have passed, in step S114, this is remounted on the turntable 12 by the robot 14. In step S115, the third container is transferred to a working area of the magnetic particle integratedly processing apparatus $15_7$. In step 116, the pipette tips 50 are inserted into each storage part of the third container and then, with the magnetic field exerted on the interior of the pipette tips 50, the mixed liquid is sucked, and with the magnetic particles attached to the inner wall of the pipette tips 50 and thus separated, the pipette tips 50 are raised.

Then the third container with the residual liquid stored therein, is transferred by the turntable 12 and the robot 14 to the stacking apparatus $15_1$, in order to be removed. Once the fourth container has been transferred by the turntable 12 to a work area of the magnetic particle integratedly processing apparatus $15_7$, the pipette tips 50 with the magnetic particles attached to their inner walls are inserted into each storage part, and sucking and discharge is repeatedly performed in 50 μl of a 70% ethanol solution with the magnetic field removed, to re-suspend the magnetic particles.

In step S117, when the fourth container is moved by the turntable 12 to near one of the constant temperature apparatus $15_2$ to $15_5$, in step S118, it is transferred by the robot 14 to one of the constant temperature apparatus $15_2$ to $15_5$ held at 80° C. to 90° C., and left for two minutes.

In step S119, after two minutes have passed, then in step S120, the fourth container is mounted on the above turntable 12 by the robot 14, and in step S121, the fourth container is transferred to a work area of the magnetic particle integratedly processing apparatus $15_7$. Then in step S122 the pipette tips 50 are sucked while inserted into each storage part of the fourth container with the magnetic field applied so that the magnetic particles are separated by being attached to the inner wall, and in this condition, the pipette tips 50 are raised.

Thus the fourth container is transferred with the residual ethanol solution stored therein and then removed. Next when the fifth container has been transferred to a work area of the magnetic particle integratedly processing apparatus $15_7$, the pipette tips 50 with the magnetic particles attached to their inner walls are inserted into each storage part, and sucking and discharge is repeatedly performed in 2 to 5 μl of the loading buffer solution with the magnetic field removed, to re-suspend the magnetic particles. After this, the suspended liquid is sucked with the magnetic field applied, and the magnetic particles are attached to the inner wall of the pipette tips 50, and thus separated and removed, so that a cleaned up product is created in the fifth container.

In step S123, the fifth container is transferred to the vicinity of the stacking apparatus $15_1$ by the turntable 12, and in step S124, is stacked in the stacking apparatus $15_1$ by the robot 14 to be used for the next process.

As described above, these processes are able to prevent cross-contamination completely by using the 96 piece tips and 5 layer plate-shaped containers for 96 samples. In this case, six container mounting positions including a tip rack are used on the turntable 12. Since the turntable 12 has twelve container mounting positions, then in this embodiment, by adjusting the incubation time, execution is possible where two processes are performed together at the same time.

In the above example, the processing involves using removable pipette tips at the nozzles. Instead of this processing, by including a step for washing the dispensing tips and washing the containers, the used mounting positions on the turntable 12 can be reduced, and the number of processes performed together at the same time can be increased.

Figure 10:
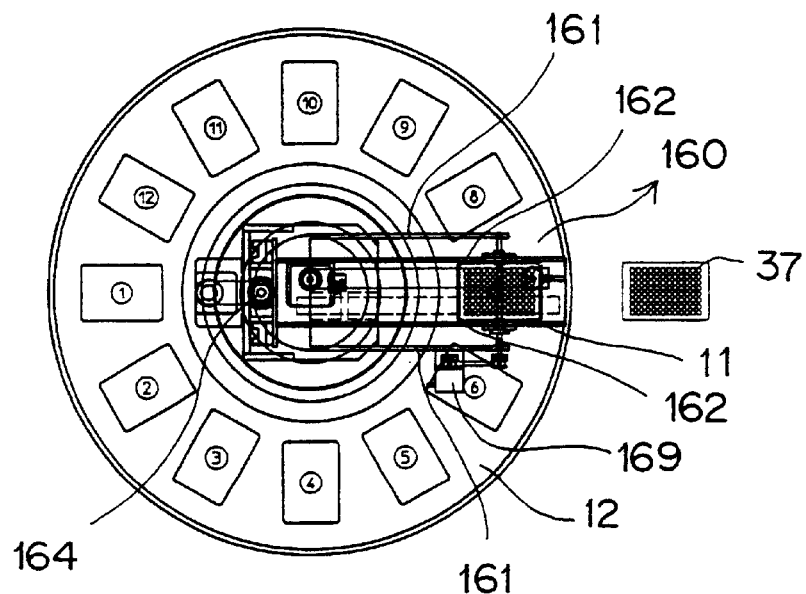
FIG. 10 is a view showing another container transfer and processing apparatus which uses a robot, according to an embodiment of the present invention.
Figure 10:
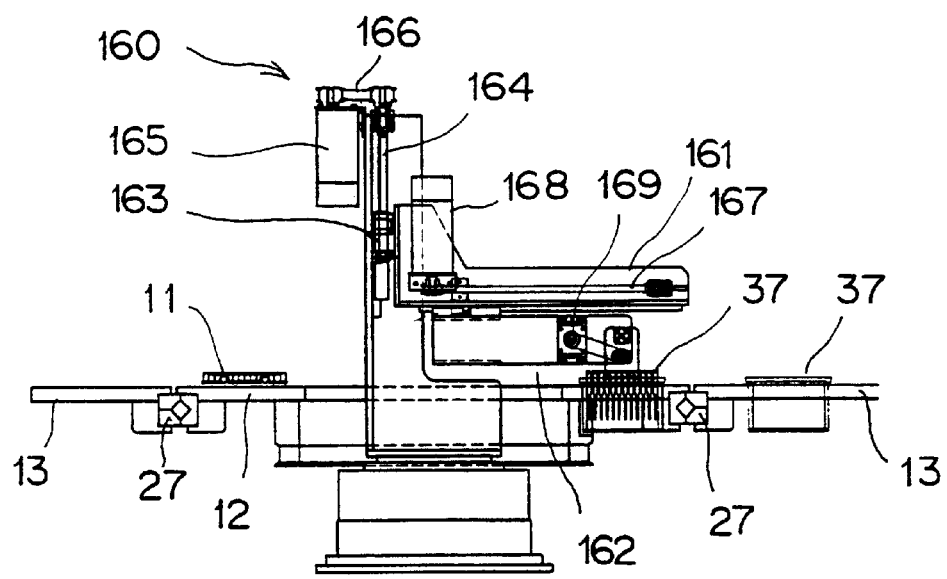

FIG. 10 shows a container transfer and processing system according to another embodiment.

The container transfer and processing system uses a polar coordinate type robot 160 instead of the polyarticulate type robot 14.

The robot 160 is installed inside the inner area of the turntable 12, and has a rotation shaft provided concentric with a rotation center of the turntable. The robot 160 has an arm 161 which is installed along the radial direction from the rotation center above the turntable. 12 and a hand part 162 which is installed under the arm 161 for holding plate-shaped containers tightly from their sides in a perpendicular direction to the longitudinal direction of the arm 161.

A nut 163 is attached to the arm 161, and the nut 163 is threaded with a ball screw 164 which is provided along the vertical direction. The ball screw 164 is rotated and driven by a motor 165 through a timing belt 166 to thereby move the arm 161 in the vertical direction.

The hand part 162 is connected to the nut which is threaded with the ball screw 164 provided on the arm 161, and is provided so that by rotation drive of the motor 168, the hand part 162 can be moved back and forth in the radial direction of the turntable 12. The hand part 162 is provided so as to be movable in the perpendicular direction to the longitudinal direction of the arm 171 by an air cylinder 169, and can thus hold an object tightly. The container transfer and processing system using the robot 160 according to this embodiment is suitable for smaller scale operations compared to using the polyarticulate robot 14.

Figure 11:
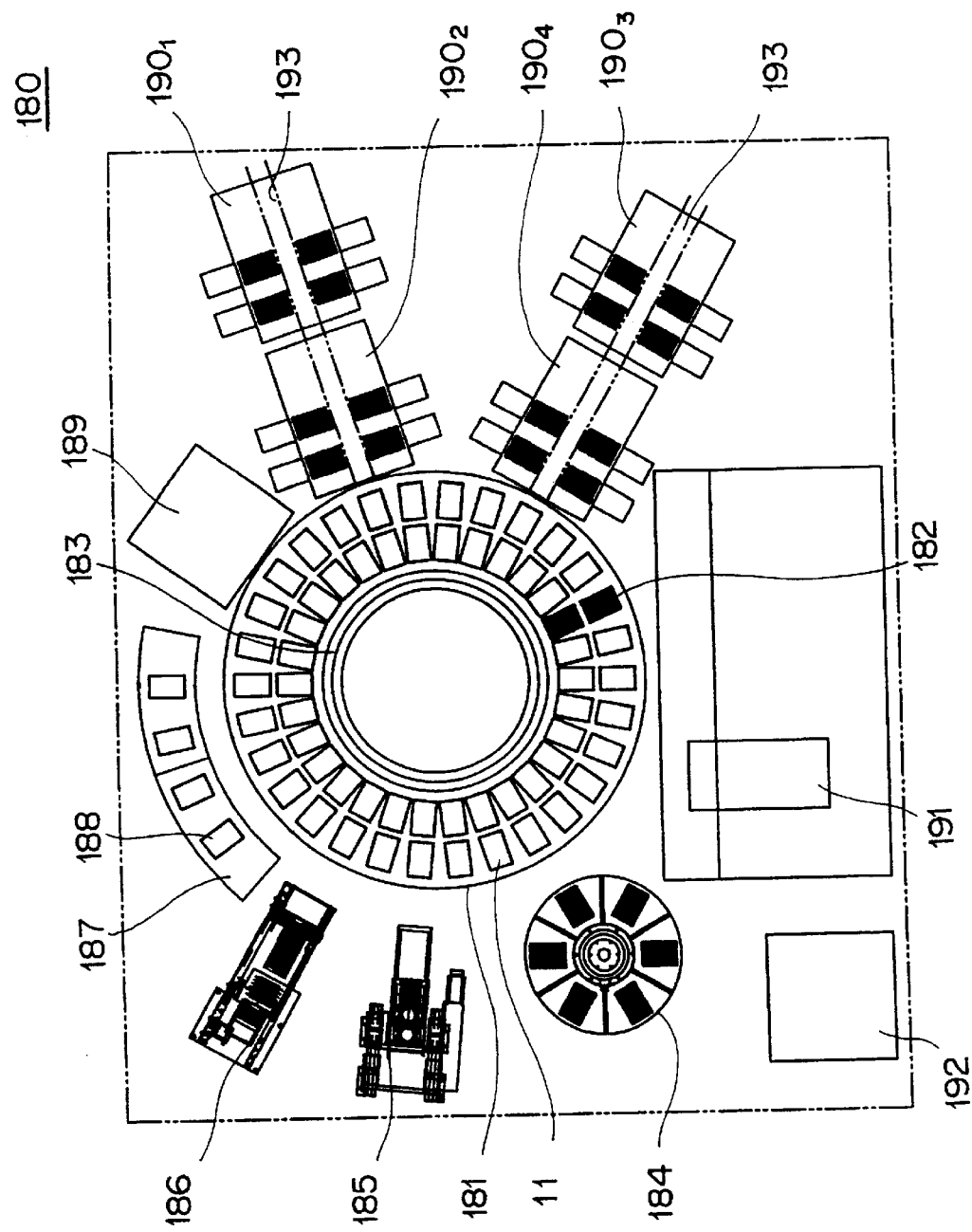
FIG. 11 is a view showing the container transfer and processing apparatus according to the embodiment of the present invention.
Figure 12:
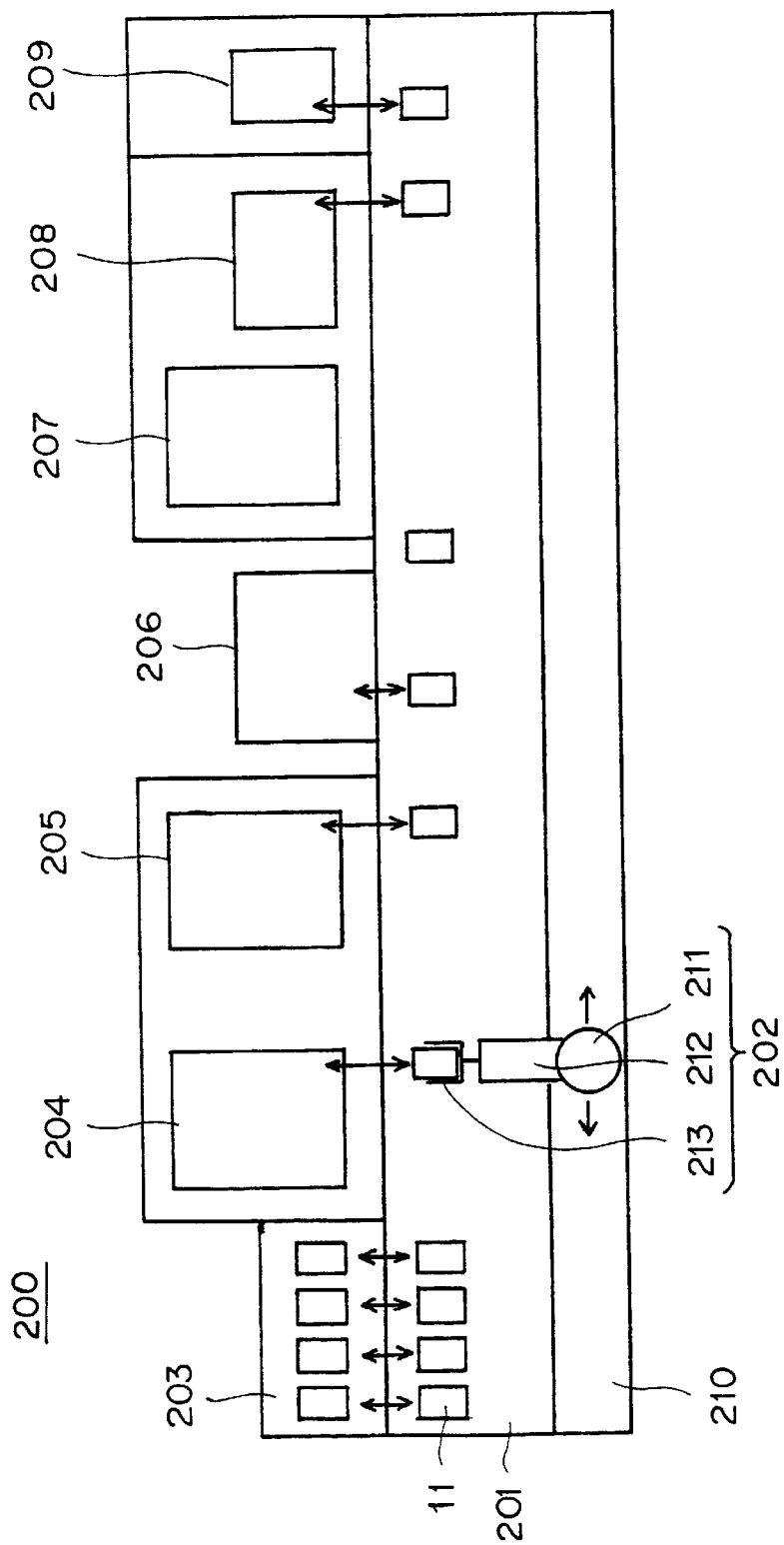
FIG. 12 is a view showing a container transfer and processing apparatus according to a conventional example.

FIG. 11 shows a container transfer and processing system 180 according to another embodiment.

The container transfer and processing system 180 is a system suitable for when the number of containers for transfer is much more than for the container transfer and processing system according to the aforementioned embodiment.

The container transfer and processing system 180 differs from the container transfer and processing system 10 in that a total of 60 containers with the containers 11 in two concentric rows with 30 containers per row, are mounted on a turntable 181 being a simultaneous transfer device. Moreover, it is also possible to mount tip racks 182 onto the turntable 181, besides the containers 11.

Furthermore, inside the transfer route of the turntable 181, a robot (not shown in the figure) is provided so as to be movable along a closed rail 183 which is laid in a circular shape. Moreover, in the outside area of the turntable 181, a variety of types of apparatus serving as the set of container working devices are arranged along the route.

The container working device has; a rotation type micro stacker 184 for stacking the plate-shaped containers 11, an integrated processing apparatus 185 capable of dispensing all together to the 96 storage parts of the container 11, a dispenser 186 having an 8 head nozzle, a plate stacker 187 capable of stacking the micro plates 11 in 20 layers on a stacking part 188 under low temperature conditions, a plate reader 189 for reading information displayed on the micro plates 11, constant temperature apparatus $190_1$, $190_2$, $190_3$ and $190_4$ for keeping the micro plates at a high temperature, a dispenser 191, and a personal computer 192 for drive control. Reference symbol 193 denotes a transfer line supply part 193 for supplying containers 11 onto the turntable 181.

The contents of these embodiments are specifically described for a better understanding of this invention, and are merely illustrations not to be interpreted as limiting. Therefore, changes are possible within a scope which does not alter the gist of the invention. For example, in the above description, only the case of a turntable as a simultaneous transfer device was described. However, the invention is not limited to this case, and for example, a transfer device having a linear route, an elliptical route or a polygon shape route is also possible.

Furthermore, in the above description, the case of only one robot inside the transfer route was described. However, the case where two or more are provided is also possible. Moreover, the case was described where each plate-shaped container has 96 storage parts was described, however the invention is not limited to this case.

Furthermore, in the above description, the container working devices were eight machines, and the processing performed inside the route was only the processing related to the magnetic particle integratedly processing apparatus. However, the number of container working devices, is not limited by this case, and a case where the number is less than this, or where other kinds of container working device are added is also possible. As these devices there is for example, a PCR thermal cycler and a chemiluminescence (fluorescence, absorbancy) plate reader.

Moreover, for the processing performed inside the route, not, only that for the case of the magnetic particle integratedly processing apparatus, but other processing may be performed inside the route. As these apparatus there is an agitating apparatus for agitating material stored in the container, by shaking the container. Furthermore, by suitably overcoming obstacles to movement of the robot arm, then an operation area can be provided on the route not only for the magnetic particle integratedly processing apparatus, but also for the dispensing apparatus or the washing apparatus. Therefore, the transfer time for the robot can be reduced enabling speeding up. Furthermore, the sets of container working devices is not limited to the case where these are fixedly provided, but these may be movable to the extent necessary to avoid collision or contact with the robot.

Moreover, in the above description, only one kind of container was described. However it is also possible to use containers having many kinds of shapes to correspond to the process contents. For example, in normal processes, containers where the storage parts have round bottoms may be used, while for processes including PCR, containers having smaller diameter storage parts may be used.

What is claimed is:

1. A container transfer and processing system comprising;
    simultaneous transfer means capable of mounting a specified quantity of plate-shaped containers each having a specified quantity of storage parts, or a specified quantity of tip racks each storing a specified quantity of pipette tips, and simultaneously transferring said plate-shaped containers or said tip racks along a specified route;
    at least one container working device for performing processing operations on said containers or contents of said containers, which are within said route, and said containers or contents of said containers which are outside of said route;
    individual transfer means capable of individually transferring said containers or said tip racks independent of the state of said simultaneous transfer means with respect to arbitrary positions capable of mounting said containers or said tip racks, inside an area including the positions capable of mounting said containers on the route of said simultaneous transfer means and on said at least one container working device; and
    a control part for performing transfer of both of said transfer means and control of the operation of said at least one container working device.

2. A container transfer and processing system according to claim 1, wherein said route of said simultaneous transfer means is closed, and transfer direction is in both the forward and reverse directions along said route, and said individual transfer means is a robot which is provided in an inside area enclosed within said route, and which has a holding part capable of holding said containers or said tip racks, and an arm capable of moving said holding part within said area.

3. A container transfer and processing system according to claim 1, wherein said processing operations include stacking said containers or said tip racks, dispensing magnetic particle suspensions into said containers, supplying reagents for dispensing into said containers, mixing and stirring the contents of said containers, separating the contents of a said containers, heating said containers, washing said containers, measuring the contents of said containers, and sucking cleaning solution which has been inserted into said containers.

4. A container transfer and processing system according to claim 1, wherein said at least one container working device is a dispensing apparatus, and additional container working devices have at least one apparatus selected from; a magnetic particle integratedly processing apparatus, a measurement apparatus, a constant temperature apparatus for cooling or heating, a stacking apparatus for said containers or said tip racks, a reagent supplying apparatus, a separator, a precipitating apparatus, and a washing apparatus.

5. A container transfer and processing system according to claim 2, wherein said robot has a rotation shaft and a vertical motion shaft, both following along directions perpendicular to a transfer face of said simultaneous transfer means, within an area of said transfer means.

6. A container transfer and processing system according to claim 5, wherein the route of said simultaneous transfer means is formed in a circular shape, and the rotation shaft of said robot is provided concentric with a center of rotation of said simultaneous transfer means.

7. A container transfer and processing system according to claim 1, wherein said robot is provided so as to be moveable along a route direction of said simultaneous transfer means, within an area inside of said simultaneous transfer means.

8. A container transfer and processing system according to claim 4, wherein said dispensing apparatus has a dispenser having a plurality of liquid passages inside of which liquid passes, a magnetic force part for exerting and removing a magnetic field onto and from said liquid passages from outside, a pressure controller for controlling the pressure inside said liquid passages to suck and discharge liquid, and a moving part for relatively moving between said dispensing apparatus and said liquid passages and the containers.

9. A container transfer and processing system according to claim 4, wherein said magnetic particle integratedly processing apparatus includes a plurality of liquid passages inside of which liquid passes and which are arranged in matrix form, a magnetic force part for exerting and removing a magnetic field onto and from said liquid passages from outside, and a pressure controller for controlling the pressure inside said liquid passages to suck and discharge liquid.

10. A container transfer and processing system according to claim 9, wherein said magnetic force part is able to exert and remove a magnetic force onto and from each liquid passage interior, in a stationary condition near an outside of said liquid passages.

11. A container transfer and processing system according to claim 10, wherein said magnetic force part is able to exert and remove a magnetic force onto and from each liquid passage interior, in a stationary condition near an outside of said liquid passages, by magnetizing and demagnetizing an external member of said liquid passages which is adjacent to an outer surface of each liquid passage.

12. A container transfer and processing system according to claim 11, wherein said magnetic force part has a magnetic material member formed from a magnetic material provided with a plurality of insertion parts for taking insertion of each liquid passage, and said external member of said liquid passages is a wall part of said insertion parts.

13. A container transfer and processing system according to claim 4, wherein in said dispensing apparatus or said magnetic particle integratedly processing apparatus, a receiving tray is provided so as to be insertable and removable with respect to an area beneath liquid passages of said dispensing apparatus or said magnetic particle integratedly processing apparatus, for receiving liquid leaking from any of said liquid passages dispensing apparatus.

14. A container transfer and processing system according to claim 4, wherein said apparatus for stacking said containers or said tip racks stores said containers or tip racks stacked vertically and includes a plurality of storage parts arranged axisymmetrically, a rotation shaft provided on an axis of symmetry line position, a rotation mechanism which rotates about said rotation shaft, and a transfer mechanism for transferring said storage parts in the vertical direction based on the number of containers or tip racks stored in said storage parts.

15. A container transfer and processing system according to claim 4, wherein said apparatus for washing containers includes a plurality of liquid passages capable of insertion into each storage part of said container, an elevating mechanism for elevating said liquid passages, and a sucking and discharging mechanism for sucking and discharging liquid, and said liquid passages have an inner liquid passage and an outer liquid passage, with the outer passage passing through the inner passage and being provided protruding slightly from the outer passage at the bottom end, and said sucking and discharging mechanism is controlled so as to discharge or suck cleaning solution from said inner passage and to suck or discharge cleaning solution from said outer passage.

16. A container transfer and processing system according to claim 4, wherein said constant temperature apparatus includes a mounting part made of thermal conductive material for mounting containers, a Peltier element provided beneath said mounting part and driven by a predetermined direction current, fins provided beneath said Peltier element, and a fan provided beneath said fins, and said mounting part, Peltier element and fins are stored in a an accommodating part made of a thermal insulation material and having an opening in a top end and a bottom end, and said fan is installed in the opening in the bottom end of said accommodating part.

17. A container transfer and processing system according to claim 4, wherein said reagent supplying apparatus includes a plurality of reagent baths which are made of transparent or translucent material for storing reagents, a pipe set communicated with a reagent supply source for supplying reagent to said reagent baths, with tips inserted into said reagent baths so as to be freely inserted and removed, floats provided in said reagent baths, a light emitting part provided outside said reagent baths for irradiating light towards said reagent baths, and a light receiving part provided outside said reagent baths so as to be able to receive light from said reagent baths.

18. A container and processing system having;
   a turntable capable of mounting a specified quantity of plate-shaped containers each having a specified quantity of storage parts arranged in matrix form, or a specified quantity of tip racks each storing a specified quantity of pipette tips, and simultaneously transferring said containers or said tip racks in both a forward and reverse direction along a circular route;
   a plurality of container working devices arranged in an area outside of said route of said turntable and along the route direction, for performing processing operations on said containers mounted on said turntable or contents of said containers or containers mounted at predetermined positions outside of said turntable or contents of said containers;
   a robot provided in an inside area surrounded by said route, said robot having a holding part capable of holding said containers or said tip racks, and an arm connected to said holding part and capable of moving said holding part independent of the state of said turntable with respect to arbitrary positions capable of mounting said containers or said tip racks, inside an area including positions capable of mounting said containers on said turntable and on said container working devices; and
   a control part for performing transfer of said turntable, operation of said container working devices, and control of said robot; and
   said plurality of container working devices include a dispensing apparatus, a magnetic particle integratedly processing apparatus, a constant temperature apparatus for cooling or heating, a stacking apparatus for said containers or said tip racks, a reagent supplying apparatus, a container washing apparatus, a nozzle tip washing apparatus and a measuring apparatus for measuring the contents of said containers.

19. A container transfer and processing system comprising;
   means for receiving a first set of elements and a second set of elements, and simultaneously passing the first and second set of elements along a specified route;
   at least one device for performing operations on at least a portion of the elements that pass along the route and for performing operations on a third set of elements which are not passing along the route;
   means for transferring at least a portion of the elements from the receiving means to a position not along the route; and
   means for controlling the means and the operation performing device.

20. The system of claim 19 wherein the first set of elements include containers and elements disposed in the containers.

21. The system of claim 19 or 20 wherein the second set of elements includes tip racks.

22. The system of claim 21 wherein the second set of elements also includes pipette tips that are stored by the tip racks.

23. The system of claim 19 wherein the elements are mounted in the position.

24. The system of claim 19 wherein the transferring means is a robot which is provided in an inside area enclosed within the route, and which comprise a means for holding the elements and an arm capable of moving the held elements within the area.

25. The system of claim 24 wherein the route is circular in shape and wherein the rotation shaft of the robot is concentric with the center of the circular route.

26. The system of claim 25 wherein the robot is moveable along a route within an area inside of the circular route.

27. The system of claim 19 wherein at least a portion of the elements are containers; wherein there are a plurality of the devices; and wherein one of the devices is a dispensing apparatus for dispensing a material into the containers, and wherein another device comprises an apparatus selected from a magnetic particle integrated processing apparatus, a measurement apparatus, a constant temperature apparatus for cooling or heating, a stacking apparatus for stacking the elements, a reagent supplying apparatus, a separator, a precipitating apparatus and a washing apparatus.

28. The system of claim 27 wherein the dispensing apparatus comprises a plurality of liquid passages inside of which liquid passes, a magnetic force part for exerting and removing a magnetic field onto and from the liquid passages from outside, a pressure controller for controlling the pressure inside the liquid passages to suck and discharge liquid, and a moving part for establishing relative movement between the dispensing apparatus and the containers.

29. The system of claim 27 wherein the magnetic particle integrated processing apparatus comprises a plurality of liquid passages inside of which liquid passes and which are arranged in matrix form, a magnetic force device for exerting and removing a magnetic field onto and from the liquid passages from outside, and a pressure controller for controlling the pressure inside the liquid passages to suck and discharge liquid.

30. The system of claim 29 wherein the magnetic force device is able to exert and remove a magnetic force onto and from each liquid passage interior, in a stationary condition near an outside of the liquid passages.

31. The system of claim 29 wherein the magnetic force device is able to exert and remove a magnetic force onto and from each liquid passage interior, in a stationary condition near an outside of the liquid passages, by magnetizing and demagnetizing an external member of the liquid passages which is adjacent to an outer surface of each liquid passage.

32. The system of claim 29 wherein the magnetic force device has a magnetic material member formed from a magnetic material provided with a plurality of insertion parts for taking insertion of each liquid passage, and the external member of the liquid passages is a wall part of the insertion parts.

33. The system of claim 27 wherein a receiving tray is provided in one of the dispensing apparatus and the magnetic particle integrated processing apparatus, the tray being insertable and removable with respect to an area beneath the liquid passages of one of the dispensing apparatus and the magnetic particle integrated processing apparatus, for receiving liquid leaking from any of the liquid passages dispensing apparatus.

34. The system of claim 27 wherein the stacking apparatus comprises a rotation shaft provided on an axis of symmetry line position, a rotation mechanism which rotates about the rotation shaft, and a transfer mechanism for transferring the storage parts in the vertical direction based on the number of elements stored in the storage parts.

35. The system of claim 27 wherein the apparatus for washing the containers comprises a plurality of liquid passages capable of insertion into each storage part of the containers, an elevating mechanism for elevating the liquid passages, and a sucking and discharging mechanism for sucking and discharging liquid, the liquid passages having an inner liquid passage and an outer liquid passage, with the outer passage passing through the inner passage and protruding slightly from the outer passage at the bottom end, the sucking and discharging mechanism being controlled so as to remove cleaning solution from the inner passage and from the outer passage.

36. The system of claim 27 wherein the constant temperature apparatus comprises a mounting part made of thermal conductive material for mounting containers, a Peltier element provided beneath the mounting part and driven by a predetermined direction current, fins provided beneath the Peltier element, and a fan provided beneath the fins and the mounting part, the Peltier element and fins being stored in an accommodating part made of a thermal insulation material and having an opening in a top end and a bottom end, and the fan is installed in the opening in the bottom end of the accommodating part.

37. The system of claim 27 wherein the reagent supplying apparatus comprises a plurality of reagent baths which are made of transparent or translucent material for storing reagents, a pipe set communicated with a reagent supply source for supplying reagent to the reagent baths, with tips inserted into the reagent baths so as to be freely inserted and removed, floats provided in the reagent baths, a light emitting part provided outside the reagent baths for irradiating light towards the reagent baths, and a light receiving part provided outside the reagent baths so as to be able to receive light from the reagent baths.

* * * * *